United States Patent
Johnson et al.

(10) Patent No.: US 9,782,186 B2
(45) Date of Patent: Oct. 10, 2017

(54) VASCULAR INTERVENTION SYSTEM

(71) Applicant: Covidien LP, Mansfield, MA (US)

(72) Inventors: Garrett Johnson, Costa Mesa, CA (US); Michael Louis Losordo, San Juan Capistrano, CA (US); Peter Skujins, Laguna Hills, CA (US)

(73) Assignee: Covidien LP, Mansfield, MA (US)

( * ) Notice: Subject to any disclaimer, the term of this patent is extended or adjusted under 35 U.S.C. 154(b) by 253 days.

(21) Appl. No.: 14/636,039

(22) Filed: Mar. 2, 2015

(65) Prior Publication Data

US 2015/0164666 A1     Jun. 18, 2015

Related U.S. Application Data

(63) Continuation-in-part of application No. 14/040,463, filed on Sep. 27, 2013, now Pat. No. 8,968,383.
(Continued)

(51) Int. Cl.
*A61B 17/221* (2006.01)
*A61M 25/00* (2006.01)
(Continued)

(52) U.S. Cl.
CPC .. *A61B 17/221* (2013.01); *A61B 2017/00292* (2013.01); *A61B 2017/2215* (2013.01); *A61B 2017/2905* (2013.01); *A61M 25/0053* (2013.01)

(58) Field of Classification Search
CPC ........ A61B 17/221; A61B 2017/00292; A61B 2017/2212; A61B 2017/2215;
(Continued)

(56) References Cited

U.S. PATENT DOCUMENTS 3,416,531 A   12/1968   Edwards
4,364,391 A   12/1982   Toye
(Continued)

FOREIGN PATENT DOCUMENTS

CN   102159157 A   8/2011
EP   450221 A1   10/1991
(Continued)

OTHER PUBLICATIONS

Kim, et al., "Sum of the Curve Indices for Estimating the Vascular Tortuousness of the Internal Carotid Artery," Neurointervention 2009; 4: 101-106.
(Continued)

*Primary Examiner* — Kathleen Holwerda
(74) *Attorney, Agent, or Firm* — Mark Kertz

(57) ABSTRACT

An intravascular intervention system can include a manipulation member sized for insertion into a blood vessel and an intervention member coupled to the manipulation member. The manipulation member can include a longitudinally extending tube having a helical cut extending along the tube. The helical cut can have an axial length of at least 50 cm and be continuous along the axial length. The intervention member can be compressible to a collapsed configuration for delivery to an endovascular treatment site through a catheter and be self-expandable from the collapsed configuration to an expanded configuration.

26 Claims, 19 Drawing Sheets

Related U.S. Application Data

(60) Provisional application No. 61/870,755, filed on Aug. 27, 2013.

(51) Int. Cl.
    *A61B 17/00* (2006.01)
    *A61B 17/29* (2006.01)

(58) Field of Classification Search
    CPC ...... A61B 2017/2905; A61M 25/0052; A61M 25/0053; A61M 25/0054; A61F 2/95; A61F 2/954; A61F 2/958; A61F 2/962
    See application file for complete search history.

(56) References Cited

U.S. PATENT DOCUMENTS

| | | |
|---|---|---|
| 4,425,919 A | 1/1984 | Alston, Jr. et al. |
| 4,516,972 A | 5/1985 | Samson |
| 4,655,771 A | 4/1987 | Wallsten |
| 4,723,936 A | 2/1988 | Buchbinder et al. |
| 4,790,831 A | 12/1988 | Skribiski |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,098,393 A | 3/1992 | Amplatz et al. |
| 5,108,411 A | 4/1992 | McKenzie et al. |
| 5,147,370 A | 9/1992 | McNamara et al. |
| 5,178,158 A | 1/1993 | de Toledo |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,529 A | 6/1994 | Kontos |
| 5,358,493 A | 10/1994 | Schweich, Jr. et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St. Germain et al. |
| 5,545,209 A | 8/1996 | Roberts et al. |
| 5,554,139 A | 9/1996 | Okajima |
| 5,569,220 A | 10/1996 | Webster, Jr. |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso, Jr. |
| 5,636,641 A | 6/1997 | Fariabi |
| 5,645,559 A | 7/1997 | Laptewicz, Jr. et al. |
| 5,658,264 A | 8/1997 | Samson |
| 5,662,622 A | 9/1997 | Gore et al. |
| 5,676,659 A | 10/1997 | McGurk |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio, III et al. |
| 5,743,876 A | 4/1998 | Swanson |
| 5,759,173 A | 6/1998 | Preissman et al. |
| 5,772,641 A | 6/1998 | Wilson |
| 5,782,811 A | 7/1998 | Samson et al. |
| 5,791,036 A | 8/1998 | Bronson et al. |
| 5,795,341 A | 8/1998 | Samson |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | van Muiden |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock, III et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,971,975 A | 10/1999 | Mills et al. |
| 5,984,963 A | 11/1999 | Loomis et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,083,152 A | 7/2000 | Strong |
| 6,093,177 A | 7/2000 | Javier, Jr. et al. |
| 6,105,651 A | 8/2000 | Leanna |
| 6,106,510 A | 8/2000 | Lunn et al. |
| 6,106,540 A | 8/2000 | White et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren et al. |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |

(56) References Cited

U.S. PATENT DOCUMENTS

| | | |
|---|---|---|
| 6,468,298 B1 | 10/2002 | Pelton |
| 6,475,184 B1 | 11/2002 | Wang et al. |
| 6,494,907 B1 | 12/2002 | Bulver et al. |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Sonderskov |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Akram et al. |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 | 12/2003 | Wallace et al. |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,939,337 B2 | 9/2005 | Parker et al. |
| 6,939,353 B2 | 9/2005 | Que et al. |
| 6,945,970 B2 | 9/2005 | Pepin |
| 6,960,227 B2 | 11/2005 | Jones et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,163,523 B2 | 1/2007 | Devens, Jr. et al. |
| 7,166,088 B2 | 1/2007 | Heuser |
| 7,166,099 B2 | 1/2007 | Devens, Jr. |
| 7,166,100 B2 | 1/2007 | Jordan et al. |
| 7,172,575 B2 | 2/2007 | El-Nounou et al. |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens, Jr. |
| 7,507,229 B2 | 3/2009 | Hewitt et al. |
| 7,524,322 B2 | 4/2009 | Monstdt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | McFerran et al. |
| 7,641,646 B2 | 1/2010 | Kennedy, II |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,758,624 B2 | 7/2010 | Dorn et al. |
| 7,766,820 B2 | 8/2010 | Core |
| 7,766,896 B2 | 8/2010 | Kornkven Volk et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens, Jr. |
| 7,828,790 B2 | 11/2010 | Griffin |
| 7,867,267 B2 | 1/2011 | Sullivan et al. |
| 7,879,022 B2 | 2/2011 | Bonnette et al. |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,159,219 B2 | 4/2012 | Estrada et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,366,763 B2 | 2/2013 | Davis et al. |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 | 11/2013 | Newell et al. |
| 8,597,321 B2 | 12/2013 | Monstadt et al. |
| 8,790,387 B2 | 7/2014 | Nguyen et al. |
| 8,968,383 B1 | 3/2015 | Johnson et al. |
| 9,072,624 B2 | 7/2015 | Brown et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen Cornelius et al. |
| 2002/0049412 A1 | 4/2002 | Madrid et al. |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1* | 7/2004 | Latini ............... A61M 25/008 604/523 |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |

(56) References Cited

U.S. PATENT DOCUMENTS

| | | |
|---|---|---|
| 2004/0220585 A1 | 11/2004 | Nikolchev |
| 2004/0230285 A1 | 11/2004 | Gifford et al. |
| 2004/0260271 A1 | 12/2004 | Huyser et al. |
| 2004/0260384 A1 | 12/2004 | Allen |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | McFerran et al. |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | McFerran et al. |
| 2006/0095050 A1 | 5/2006 | Hartley et al. |
| 2006/0100687 A1 | 5/2006 | Fahey et al. |
| 2006/0116750 A1 | 6/2006 | Hebert et al. |
| 2006/0129166 A1 | 6/2006 | Lavelle |
| 2006/0178698 A1 | 8/2006 | McIntyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von Oepen et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee Roth |
| 2008/0132933 A1 | 6/2008 | Gerber |
| 2008/0140180 A1 | 6/2008 | Dolan et al. |
| 2008/0147001 A1* | 6/2008 | Al-Marashi ............ A61F 2/915 604/103.04 |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | McHugo et al. |
| 2011/0208292 A1 | 8/2011 | Von Oepen et al. |
| 2011/0224650 A1 | 9/2011 | Itou et al. |
| 2011/0288626 A1 | 11/2011 | Straubinger et al. |
| 2011/0319904 A1 | 12/2011 | Hollett et al. |

(56) References Cited

U.S. PATENT DOCUMENTS

| | | |
|---|---|---|
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1* | 3/2012 | Ferrera .................... A61F 2/01 606/198 |
| 2012/0116494 A1 | 5/2012 | Leynov et al. |
| 2012/0123511 A1 | 5/2012 | Brown |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2015/0032198 A1 | 1/2015 | Folk |
| 2015/0066128 A1 | 3/2015 | Losordo |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0164666 A1 | 6/2015 | Johnson et al. |
| 2017/0035592 A1 | 2/2017 | Haggstrom |

FOREIGN PATENT DOCUMENTS

| | | |
|---|---|---|
| EP | 775470 A1 | 5/1997 |
| EP | 1637176 A1 | 3/2006 |
| EP | 1656963 A1 | 5/2006 |
| EP | 1656963 A1 | 5/2006 |
| EP | 1698369 A1 | 9/2006 |
| EP | 2078512 A1 | 7/2009 |
| GB | 1449622 A | 9/1976 |
| GB | 2179258 A | 3/1987 |
| GB | 2179258 A | 3/1987 |
| JP | 3272716 B2 | 4/2002 |
| JP | 2005110721 A | 4/2005 |
| JP | 2006021039 A | 1/2006 |
| WO | WO-9601591 A1 | 1/1996 |
| WO | WO-01/07231 A1 | 2/2001 |
| WO | WO-01/49212 A1 | 7/2001 |
| WO | WO-01/89619 A1 | 11/2001 |
| WO | WO-02/36179 A2 | 5/2002 |
| WO | WO-2007/095031 A2 | 8/2007 |
| WO | WO-2007/117645 A2 | 10/2007 |
| WO | WO-2009/140545 A2 | 11/2009 |
| WO | WO-2009/140546 A2 | 11/2009 |
| WO | WO-2010/008571 A1 | 1/2010 |
| WO | WO-2010/027485 A1 | 3/2010 |
| WO | WO-2010/086320 A1 | 8/2010 |
| WO | WO-2010/123831 A1 | 10/2010 |
| WO | WO-2010/127838 A2 | 11/2010 |
| WO | WO-2011/014814 A2 | 2/2011 |
| WO | WO-2011/076408 A1 | 6/2011 |
| WO | WO-2011/095966 A1 | 8/2011 |
| WO | WO-2011/144351 A2 | 11/2011 |
| WO | WO-2012040240 A1 | 3/2012 |
| WO | WO-2012/158152 A1 | 11/2012 |

OTHER PUBLICATIONS

Jankowitz, et al., "Measurement of Intracranial Arteries using Digital Subtraction Angiography with an Internal Control in 85 Patients," University of Pittsburgh Medical Center, 2009.

Osborn, "Diagnostic Cerebral Angiography, 2nd Edition," 1999 Lippincott Williams & Wilkins, pp. 3-38, 31, 57-81, 83-116, 135-151, 173-194.

Sugawara, et al., "Carotid-Femoral Pulse Wave Velocity: Impact of Different Arterial Path Length Measurements," Artery Res, Mar. 2010, 4(1): 27-31.

Covidien's Pipeline Embolization Device and Delivery System Product Description and Instructions for Use, Jun. 2010.

U.S. Appl. No. 14/635,456, filed Mar. 2, 2015.

U.S. Appl. No. 14/541,094, filed Mar. 15, 2015.

DuPont Product and Properties Handbook Teflon FRP Jan. 1998, accessed Jun. 14, 2016 from http:/www.rjchase.com/fep_handbook.pdf.

International Search Report and Written Opinion dated Jun. 13, 2016; International Application No. PCT/US2016/020382; 12 pages.

Plastics International Hardness Scale—Durometer Comparisons of Materials 2016, accessed Jun. 14, 2016 from http:/www.plasticsintl.com/polyhardness.htm.

Thermal tech Equipment Shore Durometer Conversion Chart, accessed Jun. 14, 2016 from http:/www.ttequip/knowledgelibrary/TechPageShoreDurometerConversionChart.htm.

International Search Report and Written Opinion from PCT/US2014/050270 dated Nov. 18, 2014.

Misumi Properties and Characteristics—Polyurethane—Tensile Strength http://us.misumiec.com/maker/misumi/mech/ roduct/ur/detail.html accessed Apr. 19, 2016.

Wikipedia Polyether block amide—Tensile Strength https://en.wikipedia.org/wiki/polyether_block_amide accessed Apr. 19, 2016.

WS Hampshire Inc. Typical Properties of PTFE—Tensile Strength; http://catalog.wshamshire.com/asset/psg_teflon_ptfe.pdf accessed Apr. 19, 2016.

\* cited by examiner

VASCULAR INTERVENTION SYSTEM

CROSS-REFERENCE TO RELATED APPLICATIONS

This application is a continuation-in-part of U.S. patent application Ser. No. 14/040,463, filed on Sep. 27, 2013, which claims the benefit of U.S. Provisional Application No. 61/870,755, filed Aug. 27, 2013, the entirety of each of which is expressly incorporated herein by reference.

BACKGROUND

Blood vessels can become partially or completely occluded by emboli, e.g., thrombi, thereby impeding or disrupting the flow of blood therethrough. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

At least one aspect of the disclosure provides methods and apparatuses for advancing an intervention member (e.g., a thrombus retrieval device, such as a stent or mesh device) using a delivery or core member to an endovascular treatment site in the body.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Clause 1. A medical device comprising: a manipulation member comprising a tubular member having an elongate tubular body and a continuous helical cut extending along the body, the cut having an axial length of at least 50 cm, the cut comprising first and second helical slots joined by a connection aperture, wherein a pitch of the cut varies along the first and second helical slots; and an intervention member configured for mobilizing thrombus, the intervention member being coupled to a distal portion of the manipulation member and advanceable via the manipulation member.

Clause 2. The device of Clause 1, wherein a segment of the cut is configured such that the pitch of the cut changes in magnitude, at both ends of the segment, by 0.2 mm/rotation or less.

Clause 3. The device of Clause 2, wherein the segment is located 10 cm or more from an endpoint of the cut.

Clause 4. The device of Clause 2, wherein the segment is located 20 cm or more from an endpoint of the cut.

Clause 5. The device of Clause 2, wherein the length of the segment is about 5 mm or less.

Clause 6. The device of Clause 2, wherein the pitch of the cut changes in magnitude at both ends of the segment, by 0.1 mm/rotation or less.

Clause 7. The device of any of the previous Clauses, wherein the cut comprises a third helical slot, joined to the second helical slot by a second connection aperture.

Clause 8. The device of Clause 7, wherein the pitch of the cut varies along the third helical slot.

Clause 9. The device of any of the previous Clauses, wherein the tube has a diameter of 2.3 mm or less.

Clause 10. The device of any of the previous Clauses, wherein the tube has a wall thickness of 0.010" or less.

Clause 11. The device of any of the previous Clauses, wherein the first and second helical slots each have an axial length of less than or equal to about 15 cm.

Clause 12. The device of any of the previous Clauses, wherein the intervention member comprises a mesh having a plurality of cells in a generally tubular configuration.

Clause 13. The device of any of the previous Clauses, wherein the intervention member comprises an expandable body having a plurality of struts.

Clause 14. The device of Clause 13, wherein the struts include radially peripherally located struts.

Clause 15. The device of Clause 13, wherein the struts include radially transversely extending struts.

Clause 16. The device of any of the previous Clauses, wherein the intervention member comprises at least one expandable wire.

Clause 17. The device of any of the previous Clauses, wherein the intervention member comprises a longitudinally connected plurality of expandable bodies.

Clause 18. The device of any of the previous Clauses, wherein the intervention member is substantially permanently coupled to the manipulation member.

Clause 19. The device of any of the previous Clauses, wherein the intervention member is coupled to a distal tip of the manipulation member and extends distally from the distal tip.

Clause 20. The device of any of the previous Clauses, wherein the intervention member comprises a thrombus removal device.

Clause 21. A vascular intervention system sized for insertion into a blood vessel, the system comprising a manipulation member and an intervention member coupled to the manipulation member, the manipulation member comprising a tube with plurality of slots connected in an end-to-end manner to form a continuous helical void extending along the length of the tube, wherein adjoining slots intersect with a connection aperture extending through a wall of the tube and having a diameter greater than respective widths of the adjoining slots, the intervention member being configured for mobilizing thrombus.

Clause 22. The system of Clause 21, wherein a pitch of the helical void varies along the length of the tube.

Clause 23. The system of any of the Clauses 21 to 22, wherein a segment of the void is configured such that the pitch of the void changes in magnitude, at both ends of the segment, by 0.2 mm/rotation or less.

Clause 24. The system of Clause 23, wherein the pitch of the void changes in magnitude at both ends of the segment, by 0.1 mm/rotation or less.

Clause 25. The system of Clause 23, wherein the length of the segment is 5 mm or less.

Clause 26. The system of Clause 23, wherein the length of the segment is 3 mm or less.

Clause 27. The system of Clause 23, wherein the length of the segment is 2 mm or less.

Clause 28. The system of Clause 23, wherein the length of the segment is about 1.0 mm.

Clause 29. The system of any of the Clauses 23 to 28, wherein the segment is located 10 cm or more from an endpoint of the void.

Clause 30. The system of any of the Clauses 23 to 28, wherein the segment is located 20 cm or more from an endpoint of the void.

Clause 31. The system of any of the Clauses 23 to 28, wherein the segment is located 30 cm or more from an endpoint of the void.

Clause 32. The system of any of the Clauses 23 to 31, wherein the segment is a first segment, and the pitch of the void changes in magnitude from the first segment to an adjacent second segment by 0.1 mm/rotation or less.

Clause 33. The system of any of the Clauses 23 to 31, wherein the segment is a first segment, and the pitch of the void changes in magnitude from the first segment to an adjacent second segment by 0.01 mm/rotation or less.

Clause 34. The system of any of the Clauses 23 to 31, wherein the segment is a first segment, and the pitch of the void changes in magnitude from the first segment to an adjacent second segment by 0.005 mm/rotation or less.

Clause 35. The system of any of the Clauses 21 to 34, wherein each of the plurality of slots has an axial length of less than or equal to about 15 cm.

Clause 36. The system of any of the Clauses 21 to 35, wherein the intervention member comprises a mesh having a plurality of cells in a generally tubular configuration.

Clause 37. The system of any of the Clauses 21 to 36, wherein the intervention member comprises an expandable body having a plurality of struts.

Clause 38. The system of Clause 37, wherein the struts include radially peripherally located struts.

Clause 39. The system of Clause 37, wherein the struts include radially transversely extending struts.

Clause 40. The system of any of the Clauses 21 to 39, wherein the intervention member comprises at least one expandable wire.

Clause 41. The system of any of the Clauses 21 to 40, wherein the intervention member comprises a longitudinally connected plurality of expandable bodies.

Clause 42. The system of any of the Clauses 21 to 41, wherein the intervention member is substantially permanently coupled to the manipulation member.

Clause 43. The system of any of the Clauses 21 to 42, wherein the intervention member is coupled to a distal tip of the manipulation member and extends distally from the distal tip.

Clause 44. The system of any of the Clauses 21 to 43, wherein the intervention member comprises a thrombus removal device.

Clause 45. A treatment method, comprising: inserting a vascular intervention system into a blood vessel, the system comprising: a manipulation member having a tubular member; and an intervention member coupled to the manipulation member, the tubular member having an elongate tubular body and a continuous helical cut extending along the body, the cut having an axial length of at least 50 cm, the cut comprising first and second helical slots joined by a connection aperture, wherein a pitch of the cut varies along the first and second helical slots; engaging a thrombus in the blood vessel with the intervention member; and moving the thrombus in a proximal direction in the blood vessel with the intervention system.

Clause 46. The method of Clause 45, further comprising removing the thrombus from the blood vessel with the intervention system.

Clause 47. The method of Clause 46, further comprising gripping the thrombus with the intervention member.

Clause 48. The method of Clause 46, wherein removing the thrombus comprises retracting the intervention member proximally via the manipulation member.

Clause 49. The method of any of the Clauses 45 to 48, further comprising advancing a catheter into the blood vessel, wherein the inserting comprises inserting the system into a lumen of the catheter.

Clause 50. The method of Clause 49, wherein the advancing a catheter comprises advancing a distal end of the catheter through the thrombus in the blood vessel.

Clause 51. The method of Clause 50, wherein engaging the thrombus in the blood vessel with the intervention member comprises proximally retracting the catheter relative to the intervention member to permit the intervention member to radially expand within the blood vessel to engage the thrombus.

Clause 52. The method of any of the Clauses 45 to 51, wherein a segment of the cut is configured such that the pitch of the cut changes in magnitude, at both ends of the segment, by 0.2 mm/rotation or less.

Clause 53. The method of Clause 52, wherein the segment is located 10 cm or more from an endpoint of the cut.

Clause 54. The method of Clause 52, wherein the segment is located 20 cm or more from an endpoint of the cut.

Clause 55. The method of any of the Clauses 52 to 54, wherein the length of the first segment is 5 mm or less.

Clause 56. The method of any of the Clauses 52 to 55, wherein the pitch of the cut changes in magnitude at both ends of the segment, by 0.1 mm/rotation or less.

Clause 57. The method of any of the Clauses 45 to 55, wherein the cut comprises a third helical slot, joined to the second helical slot by a second connection aperture.

Clause 58. The method of Clause 57, wherein the pitch of the cut varies along the third helical slot.

Clause 59. The method of any of the Clauses 45 to 58, wherein the tube has a diameter of 2.3 mm or less.

Clause 60. The method of any of the Clauses 45 to 59, wherein the tube has a wall thickness of 0.010" or less.

Clause 61. The method of any of the Clauses 45 to 60, wherein the first and second helical slots each have an axial length of less than or equal to about 15 cm.

Clause 62. A medical device comprising: a manipulation member comprising a tubular member having an elongate tubular body and a continuous helical cut extending along the body, the cut having an axial length of at least 50 cm, the cut comprising first and second helical slots joined by a connection aperture, wherein a pitch of the cut varies along the first and second helical slots; and means for gripping thrombus, the gripping means being coupled to a distal portion of the manipulation member and advanceable via the manipulation member.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

In some embodiments, various systems and devices are provided that can enable a clinician to target an endovascular site to treat the site. The system can comprise a core assembly, pusher component, or manipulation member that can be used to control an intervention member coupled (either directly or indirectly) thereto. The coupling can be permanent or releasable. The intervention member can be configured to retrieve a bodily mass or other structure within the vasculature or to be released into the vasculature as a flow restoration treatment. For example, the intervention member can retrieve a thrombus in a patient experiencing acute ischemic stroke. Further, methods of recapturing or retrieving a thrombus or other structure or obstruction within a bodily lumen are also provided. The manipulation member can extend through a catheter such that an operator can manipulate the intervention member, positioned within and/or distal to a distal end of the catheter, using the manipulation member at a location proximal to a proximal end of the catheter.

Intervention Systems

Figure 1:
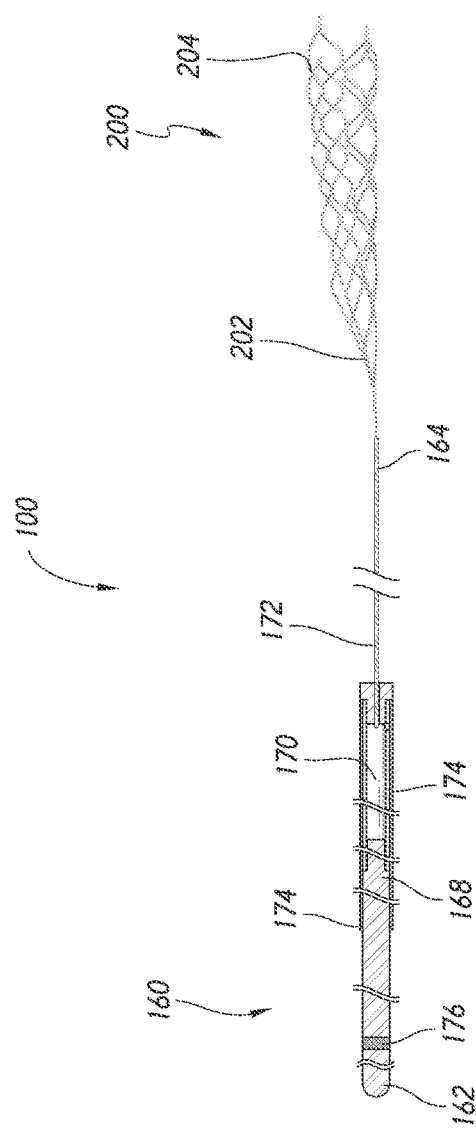
FIG. 1 is a side, cross-sectional view of an intervention system, according to some embodiments.

FIG. 1 depicts embodiments of an intervention system 100 comprising a manipulation member 160 which may be used to advance, deliver, and/or deploy a medical device, such as, but not limited to an intervention member 200, into a hollow anatomical structure such as a blood vessel. The manipulation member 160 can enable a clinician to operate or control the intervention member 200.

The manipulation member 160 can have a proximal end section 162, which can be graspable by a clinician during use, and a terminal or distal end section 164, which can be coupled (either directly or indirectly) to the intervention member 200. The manipulation member 160 can generally comprise any member(s) with sufficient flexibility, column strength and thin-ness to move the intervention member 200 or other medical device through a catheter. The manipulation member 160 can therefore comprise a wire, or a tube such as a hypotube, or a braid, coil, or other suitable member(s), or a combination of wire(s), tube(s), braid(s), coil(s), etc.

For example, the embodiment of the manipulation member 160 depicted in FIG. 1 is of multi-member construction, comprising a proximal wire 168, a tube 170 (e.g., a tubular member or hypotube) connected at its proximal end to a distal end of the proximal wire 168, and a distal wire 172 connected at its proximal end to a distal end of the tube 170. An outer layer 174, which can comprise a layer of lubricious material such as PTFE (polytetrafluoroethylene or TEFLON™) or other lubricious polymer(s), can cover some or all of the tube 170 and/or proximal wire 168.

The proximal and/or distal wires 168, 172 may taper or vary in diameter along some or all of their lengths. The proximal wire 168 may include one or more fluorosafe markers 176, and such marker(s) can be located on a portion of the wire 168 that is not covered by the outer layer 174, e.g., proximal of the outer layer 174. This portion of the wire 168 marked by the marker(s) 176, and/or proximal of any outer layer 174, can comprise a bare metal outer surface.

Additional features and components of the manipulation member 160 can be implemented as shown and discussed with respect to the core member 160 discussed in U.S. patent application Ser. No. 14/040,463, filed on Sep. 27, 2013, the entirety of which is expressly incorporated herein by reference.

Further, in some embodiments, the manipulation member 160 can omit or exclude one or more features illustrated in FIG. 1. For example, the distal wire 172 can be removed and a more direct connection can be created with the intervention member 200 by coupling a proximal end of the intervention member 200 with the tube 170 directly.

The intervention member 200 can comprise a proximal end portion 202 and a distal end portion 204. In some embodiments, the intervention member 200 can comprise a thrombus gripping device, a thrombus removal device, and/or a thrombus mobilization device. The intervention member 200 can be expandable by an external expansion force or be self-expandable. The intervention member 200 can comprise a generally elongate mesh or stent, such as a laser-cut stent or other form of stent such as a braided stent, roll-up stent, etc. So as to perform the function of thrombus gripping, removal or mobilization, an intervention member in the form of a stent can comprise a stentriever. Further, the intervention member 200 can comprise a foreign body retrieval component that can be configured to engage with, grasp, capture, or otherwise retrieve an implant, such as a stent, coil, graft, or other foreign structure disposed within the vasculature.

In some embodiments, the intervention member 200 can comprise an expandable body having a plurality of struts, and the struts can be interconnected to form, for example, a network of such struts that is configured to grip, engage, remove, or mobilize thrombus. The body can optionally include radially peripherally located struts, for example struts that are located in a sidewall of a generally cylindrical portion of the body when the body is in an expanded configuration, and/or radially transversely extending struts, for example struts that extend across a longitudinal end view of the body when the body is in an expanded configuration. The intervention member can comprise a longitudinally connected plurality of individual bodies, and each of such bodies can have radially peripherally located struts and/or radially transversely extending struts. The bodies of such an intervention member can be longitudinally interconnected by one or more generally longitudinally centrally located, longitudinally extending link members.

In some embodiments, the intervention member 200 can be generally tubular (e.g. a generally tubular mesh) and have an open proximal end and/or an open distal end, or a proximal end and/or distal end that is at least partially closed. Such a generally tubular intervention member can have a mesh that is elongate and/or longitudinally extending.

In some embodiments, the intervention member 200 can comprise one, or several, expandable wires, coils and/or spirals that can expand to form a space-filling shape or mass including the wire(s)/coil(s)/spiral(s) and void space encompassed thereby. The resulting shape or mass can be configured to grip, engage, remove, or mobilize thrombus.

Any of the intervention members 200 disclosed herein can optionally be connected to, or distal of, a distal tip of the manipulation member 160 (for example, the distal tip of the distal wire 172 where such distal wire is employed), and extend distally therefrom. For example, the proximal end or portion of the intervention member 200 can be so connected. The nature of the connection can be substantially permanent (as discussed herein), or detachable.

The intervention member 200 can optionally be similar to any of the versions or sizes of the SOLITAIRE™ FR Revascularization Device marketed by Covidien of Mansfield, Mass. USA.

Flexible System Components

The manipulation member 160 can optionally be of multi-member construction and can include the tube 170 which can comprise a tubular member or hypotube. The tube 170 can have a sidewall that is "uncut" or without openings or voids formed therein. Alternatively, the tube 170 can have openings, voids or cuts formed in the sidewall to enhance the flexibility of the tube. This may be done by cutting a series of slots in the sidewall along part or all of the length of the tube, or cutting or drilling a pattern of other openings in the sidewall, or cutting a spiral-shaped void in the sidewall.

In some embodiments, for example where the system is to be used in narrow and/tortuous vasculature, such as the neurovasculature, the tube 170 can be of relatively small outside diameter (e.g., 0.040" or less, or 0.030" or less, or 0.027" or less, or about 0.020"); have a relatively thin sidewall thickness (e.g., 0.0050" or less, or 0.0040" or less, or about 0.0030", or between 0.0025" and 0.0035"); and/or be of relatively long overall length (e.g., 50 cm or more, or 60 cm or more, or 70 cm or more, or 80 cm or more, or about 91 cm). Instead of or in addition to any one or combination of such dimensions, the tube can have a relatively long cut length (the length of the portion of the tube in which opening(s), void(s), cut(s), spiral(s) is/are present) of 50 cm or more, or 60 cm or more, or 70 cm or more, or 80 cm or more, or about 86 cm.

A relatively long, small-diameter and/or thin-walled spiral-cut tube offers certain advantages for use in the manipulation member 160 in narrow and/tortuous vasculature, such as the neurovasculature. The tube can be made highly flexible (or inflexible as the case may be) where necessary by use of an appropriate spiral pitch, and the column strength or "pushability" of the tube can be maintained largely independent of its flexibility, as the diameter of the tube can remain constant along its length, in contrast with a long tapering wire which must sacrifice pushability for flexibility as it narrows. The combination of high flexibility and pushability can facilitate easier navigation into difficult, tortuous vascular locations.

Figure 2:
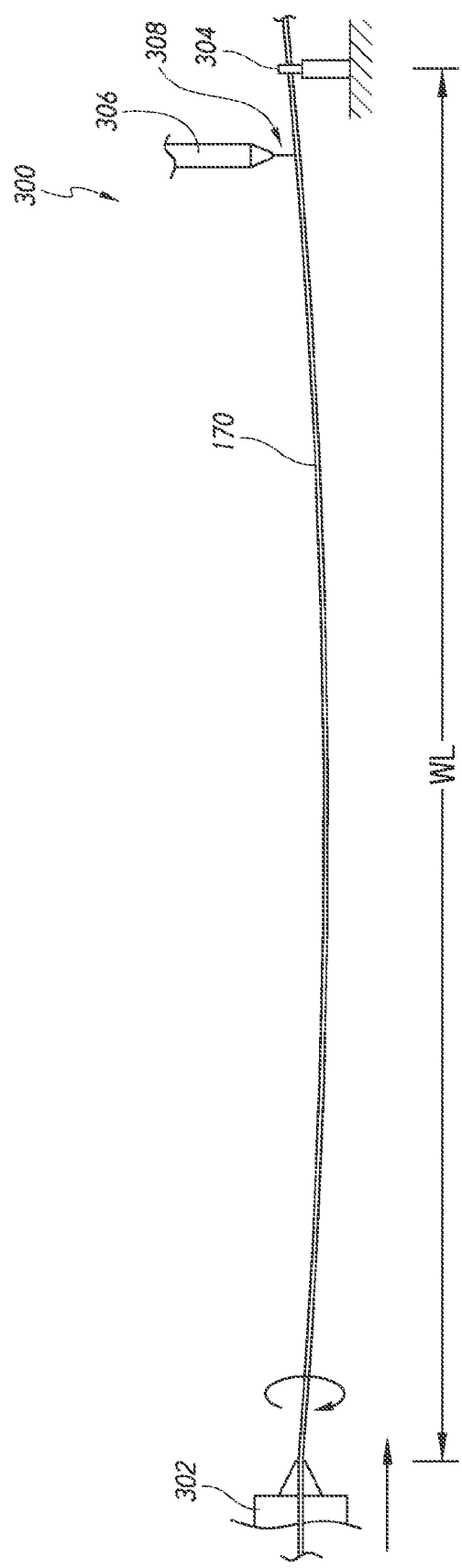
FIG. 2 is a schematic view of a laser cutting machine performing a laser cut on a catheter, according to some embodiments.

Despite these advantages, difficulties can arise when attempting to make a relatively long, small-diameter and/or thin-walled spiral-cut tube. FIG. 2 illustrates some of these difficulties in the context of a laser cutting machine 300, in which the tube 170 is supported at one end in a movable and rotatable chuck 302 and at the other end in a stationary bushing 304. A laser 306, also stationary, is positioned between the chuck 302 and the bushing 304 and oriented to emit a cutting laser beam 308 at the sidewall of the tube 170 as the tube passes by the laser 308. The chuck 302 is programmable to rotate the tube 170 and move it laterally relative to the laser beam 308 at selected rates of rotation and lateral movement, to form a spiral cut in the sidewall of the tube at a desired pitch and location. The process begins with the chuck 302 positioned at the maximum distance away from the laser 306 and bushing 304 (with a maximum working length WL of tube 170 extending therebetween), and the chuck 302 and tube 170 coupled thereto move laterally toward the laser 306 and bushing 304 while rotating until the chuck 302 reaches a minimum distance from the laser and bushing (with a minimum working length WL of tube 170 extending therebetween). However, when the working length WL of the tube 170 is long relative to its diameter and/or wall thickness, the tube 170 can sag as shown in FIG. 2, and such sag can interfere with accurate cutting of a desired spiral pattern in the tube 170. Such a long working length WL can also lead to twisting of the tube 170 over the working length, as rotational friction in the bushing 304 resists rotation of the tube 170 driven by the chuck 302. The longer the working length WL, the more the tube tends to twist as a result of friction in the bushing 304. The resulting twisting of a long tube 170 leads to torsional error in the spiral pattern cut by the laser beam 308, which can be exacerbated as the torsion repeatedly builds up in the tube 170 and is released as the torsion periodically overcomes the friction in the bushing. In these circumstances, the tube near the bushing 304 tends to rotate in "bursts" rather than at a steady rate. Finally, at an overly long working length WL the tube 170 is susceptible to buckling as it is pushed toward the bushing 304 by the chuck 302.

Figure 3:
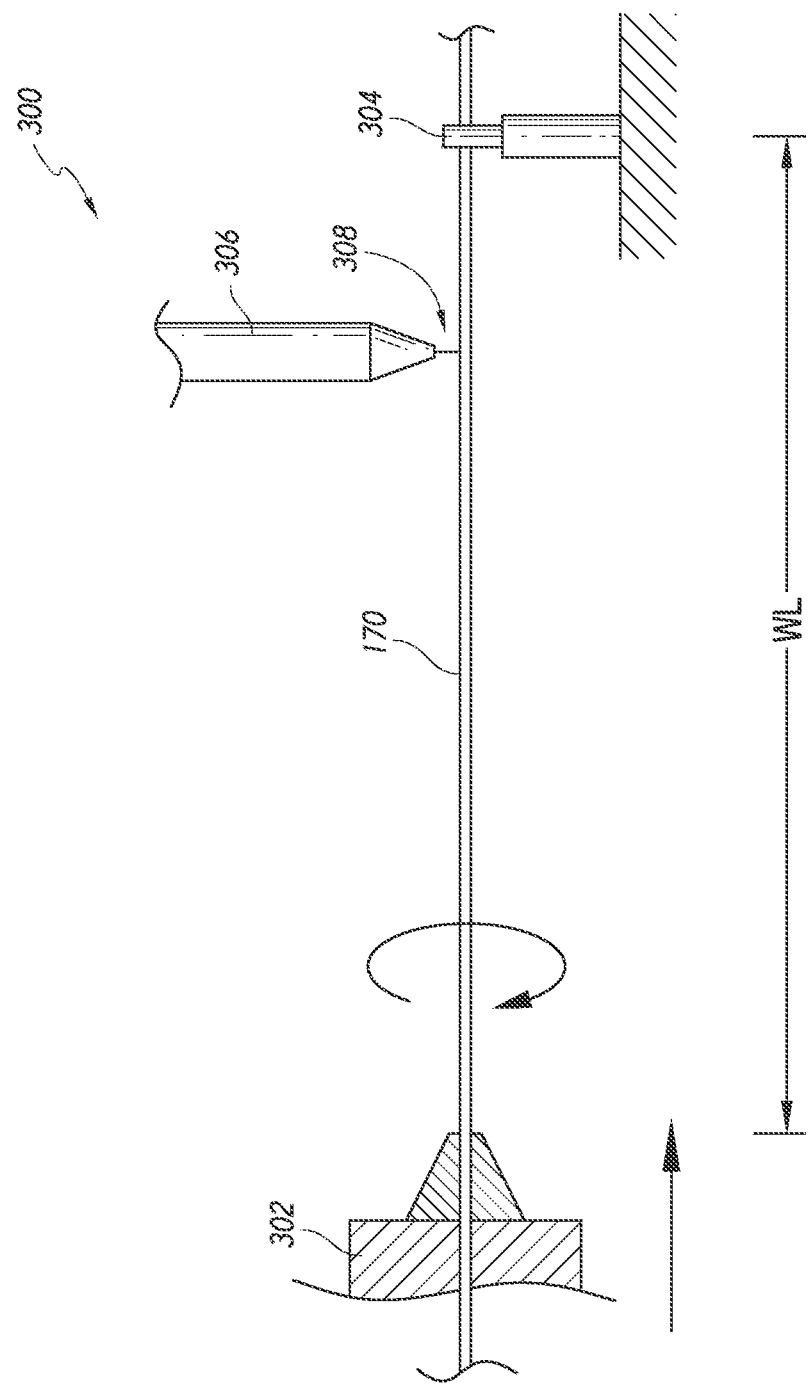
FIG. 3 is a schematic view of a laser cutting machine performing a laser cut on a catheter, according to some embodiments.

In contrast, FIG. 3 shows the benefits of a relatively short working length WL: sag, torsional error and/or buckling can be reduced or eliminated altogether. However, the inventors discovered that at the desired tube diameter and/or wall thickness the usable working length WL was much smaller than the desired overall length or cut length (e.g., 50 cm or more) of the tube 170. As an initial solution, the inventors thought to form such a longer spiral by linking together a number of separate, longitudinally adjacent spirals that are cut individually over an acceptably short working length WL. For example, five separate longitudinally adjacent cuts could be made, each at a working length of about 12 cm, in a "linked-together" fashion to form a long spiral cut of about 60 cm in length.

Figure 4:
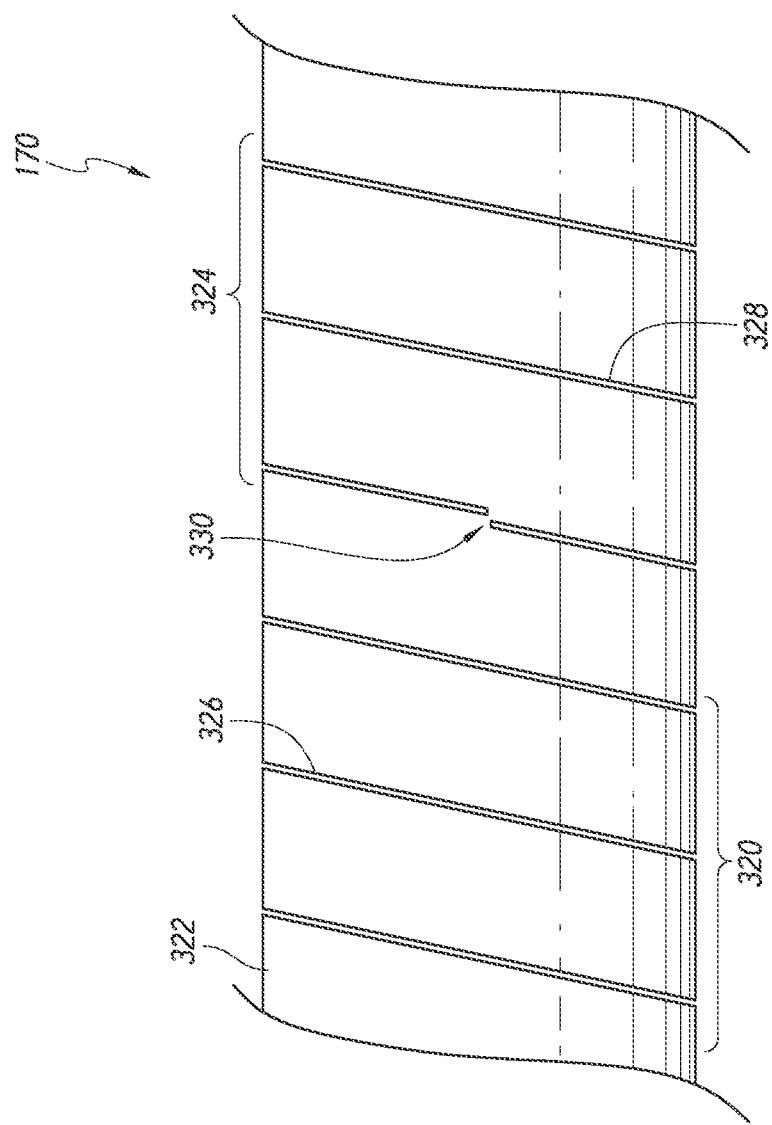
FIG. 4 is an enlarged side view illustrating drawbacks of prior art methods for creating a spiral cut in a tubular member.

FIG. 4 illustrates a problem that arises when attempting to link together separate spirals. The depicted tube 170 includes a first spiral 320 formed in the sidewall 322, and a second spiral 324 formed in the tube 170 and longitudinally adjacent to the first spiral 320. Each spiral 320, 324 comprises a respective void 326, 328 in the sidewall 322 that advances along the tube in a helical or spiraling form. The two spirals 320, 324 are longitudinally adjacent but not contiguous or continuous. Due to limitations in the laser cutting machine 300, the proximal end of the second spiral 324 cannot be positioned close enough to the distal end of the first spiral 320 to make the two spirals contiguous or continuous. Instead, the two spirals 320, 324 are separated by a discontinuity 330 between the distal end of the first spiral 320 and the proximal end of the second spiral 324. Such a discontinuity can be a source of cracks formed in the sidewall 322 when the tube 170 is subject to bending, twisting or other stresses encountered in vascular use.

Figure 5:
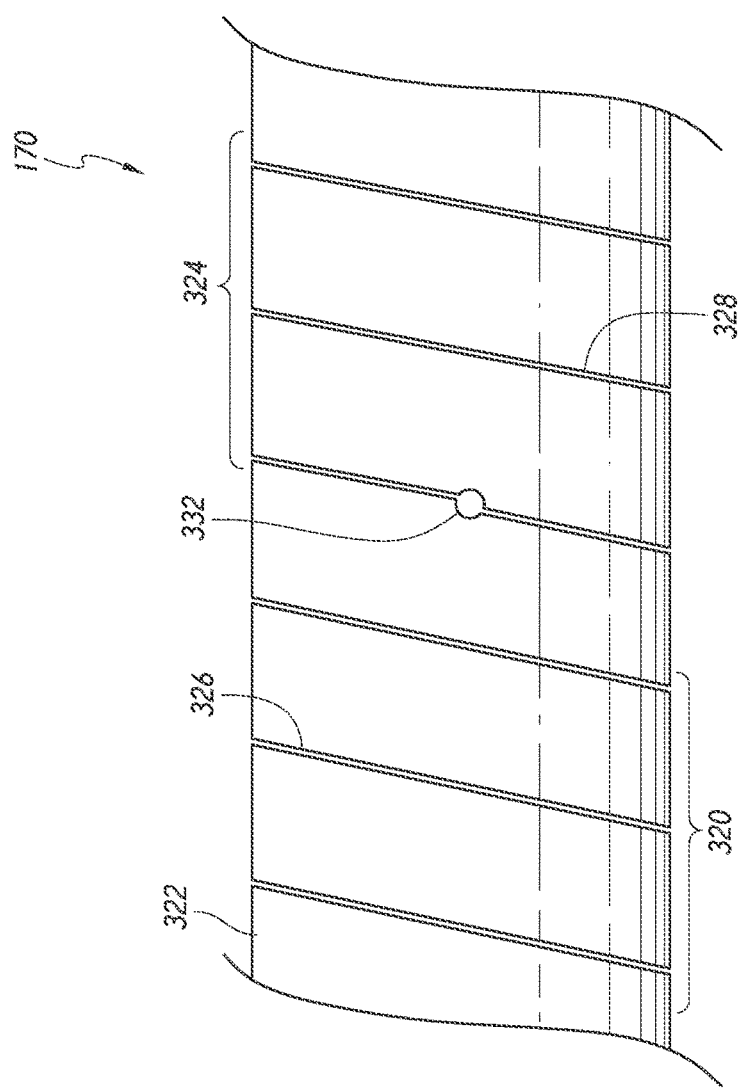
FIG. 5 is an enlarged side view of contiguous or continuous spiral cut in a tubular member, according to some embodiments.

FIG. 5 illustrates one embodiment of a solution to the problems of discontinuity and crack formation. In the embodiment of FIG. 5, the two spirals 320, 324 are formed in the same manner as in FIG. 4 but the spirals (and their respective voids 326, 328) are joined by a connection aperture 332. The connection aperture 332 can comprise an additional void that is formed (e.g., cut) in the sidewall 322 and is contiguous or continuous with the voids 326, 328 of the first and second spirals 320, 324. Accordingly, the connection aperture 332 and the voids 326, 328 can be considered to form a single, contiguous or continuous void extending along the contiguous or continuous first and second spirals 320, 324. The connection aperture 332 can comprise a circle, as shown in FIG. 5, or any other suitable shape such as an ellipse or polygon. A circle is thought to be advantageous due to a tendency to minimize the possibility of crack formation near the juncture of the voids 326, 328.

In various embodiments of the tube 170, a relatively long contiguous or continuous helical or spiral cut can be provided in the sidewall of the tube. For example, the tube 170 can have such a helical or spiral cut over any of the various cut lengths specified above or elsewhere herein for the tube 170. A tube 170 having such a helical or spiral cut have also have any one or combination of the various outside diameters, sidewall thicknesses and/or overall lengths specified above or elsewhere herein for the tube 170.

The long contiguous or continuous helical or spiral cut can be implemented as discussed herein, e.g., as with respect to FIG. 5. Two or more longitudinally adjacent spirals, cuts, slots or voids can be formed contiguously or continuously in the sidewall of the tube 170 and joined at their adjacent ends by connection aperture(s) 332 to form a spiral or helical cut, slot or void that is contiguous or continuous along the overall length or along the cut length of the tube 170. In some embodiments, the individual spirals, cuts, slots or voids can be about 15 cm in length, or 15 cm or less in length. These need not be uniform in length along the tube or cut length; for example, the first or last spiral, cut, slot or void can be made somewhat shorter in order to achieve a cut length that is not an even multiple of the length of the individual spirals.

In some embodiments, one or more terminal apertures may be employed in the spiral or helical cut, slot or void. Such terminal aperture(s) can similar to any of the connecting apertures 332 disclosed herein, with the exception that they are positioned at one or both terminal ends of the spiral rather than at a juncture of two or more individual spirals. In still other embodiments of the tube 170, a spiral or helical cut, slot or void is employed with terminal aperture(s) at one or both terminal ends and no connecting apertures along the cut length. One or multiple such spirals may be formed in the sidewall 322 of a single tube 170. Where employed, the terminal aperture(s) can serve as a stress relief or measure against sidewall crack formation at the end(s) of the spiral. A terminal aperture can be an aperture extending radially through the tube 170 (e.g., configured similarly to the connecting aperture 332), but positioned at an end of a given spiral that is not between the given spiral and another spiral.

Instead of or in addition to a spiral that is contiguous or continuous over a relatively long overall length or cut length of the tube 170, the pitch of the spiral can be controlled precisely over a long overall length or cut length. For example, the pitch of the spiral can vary over the cut length such that a pitch of a specific magnitude can prevail along a relatively short segment of the cut length, for example 5 mm or less, or 3 mm or less, or 2 mm or less, or about 1.0 mm. In this manner, the spiral pitch can be finely adjusted in small increments of the cut length thereby facilitating superior control over the mechanical properties of the tube 170 (e.g., bending stiffness, column strength) in various portions of the tube. Therefore, the tube 170 can have a pitch that varies in magnitude (including a specific "first pitch magnitude") along the overall length or cut length of the tube, and the first pitch magnitude can prevail along a first segment of the cut length. The first segment can have a length (measured along the axis A-A) of 5 mm or less, or 3 mm or less, or 2 mm or less, or about 1.0 mm. The magnitude of the pitch can change from the first magnitude at one or both ends of the first segment. The first segment can be located (e.g., in a contiguous or continuous void) anywhere along the cut length, including location(s) relatively far from the endpoints of the cut length, e.g., more than 10 cm away, or more than 20 cm away, or more than 30 cm away from an endpoint of the cut length.

Instead of or in addition to achievement of a particular pitch magnitude in one or more short segments of the cut length (and/or a spiral that is contiguous or continuous over a relatively long overall length or cut length of the tube 170), the pitch magnitude can be controlled precisely so that it can vary in relatively small increments. (The pitch can be expressed in mm/rotation.) For example, the pitch can vary in magnitude by 0.2 mm/rotation or less, or 0.1 mm/rotation or less, or 0.01 mm/rotation or less, or 0.005 mm/rotation or less. Thus is provided another manner in which the spiral can be finely controlled to facilitate desired mechanical properties in various portions of the tube 170. Therefore, the tube 170 can have a pitch that varies in magnitude (including a specific "first pitch magnitude") along the overall length or cut length of the tube, and the first pitch magnitude can prevail along a first segment of the cut length. The magnitude of the pitch can change from the first magnitude by 0.2 mm/rotation or less, or 0.1 mm/rotation or less, or 0.01 mm/rotation or less, or 0.005 mm/rotation or less, at one or both ends of the first segment. The first segment can be located (e.g., in a contiguous or continuous void) anywhere along the cut length, including location(s) relatively far from the endpoints of the cut length, e.g., more than 10 cm away, or more than 20 cm away, or more than 30 cm away from an endpoint of the cut length.

In one embodiment, the tube 170 has an overall length of 91 cm, cut length of 86 cm, outside diameter of 0.020", wall thickness of 0.003", spiral cut (slot) width of 25 microns, circular connection apertures with a diameter of 100 microns, and individual spiral cut lengths of about 15 cm.

Figure 6:
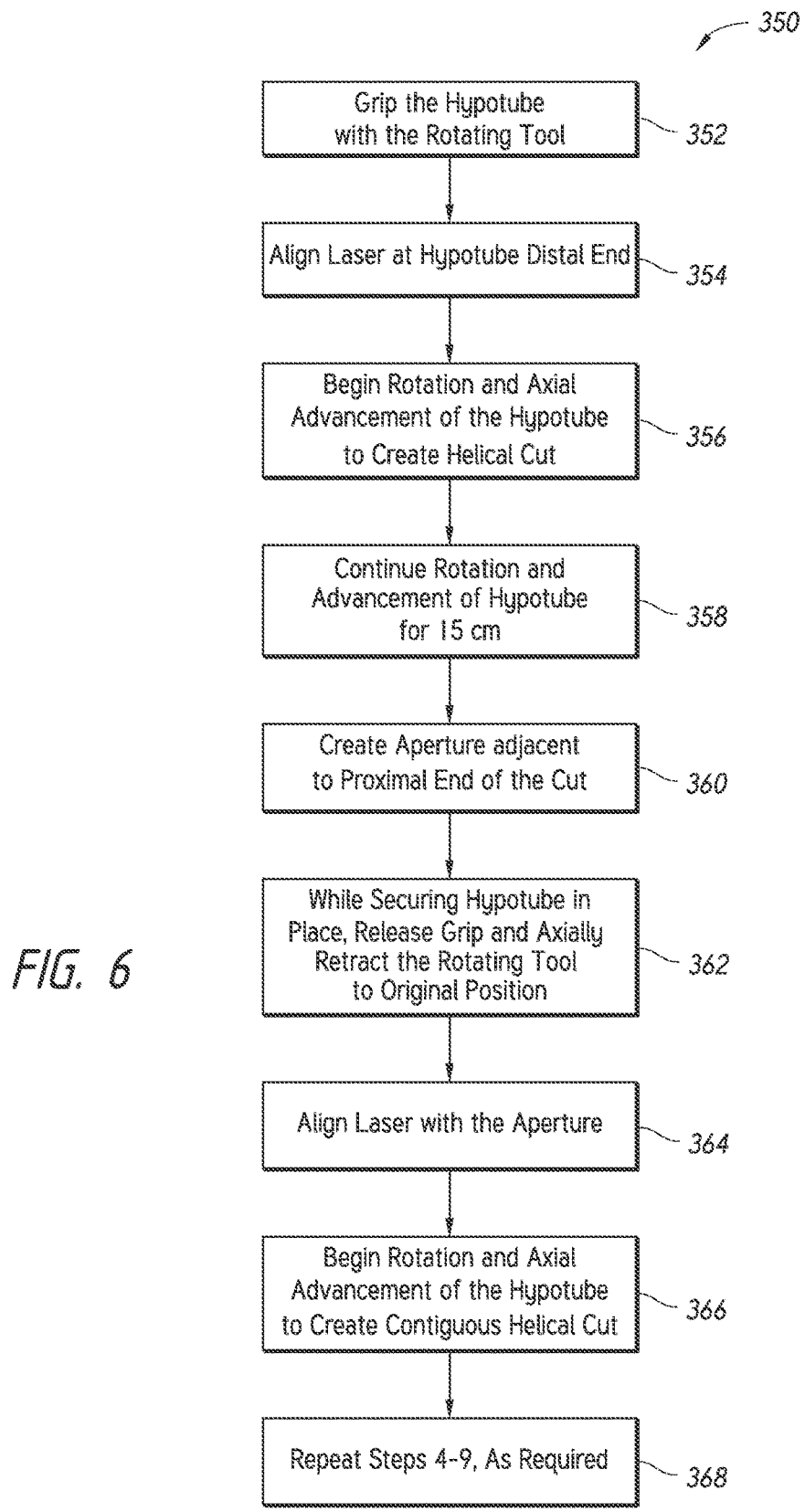
FIG. 6 is a flowchart illustrating representative steps of a method of performing a helical cut in a tubular member, according to some embodiments.

FIG. 6 depicts in flowchart form one embodiment of a method 350 of forming a relatively long spiral cut in the sidewall 322 of the tube 170, using equipment such as the laser cutting machine 300 described herein with reference to FIGS. 2 and 3. The method 350 begins at 352 by gripping the tube 170 with a rotating tool such as the chuck 302, followed at 354 by aligning or aiming the laser 306 with or at a portion of the tube 170, such as one of the proximal and distal ends thereof. Next, at 356, rotation and axial (lateral) advancement of the tube 170 relative to the laser 306 is commenced, at rates selected to obtain the desired spiral pitch, with the rotating tool or chuck 302. In this manner the laser 306 begins to cut a helical or spiral void in the sidewall of the tube 170. This is continued at 358 until the void has been formed along the desired spiral segment length (e.g., 15 cm, or 15 cm or less). At 360, once the terminal end of the spiral segment has been formed, the rotating tool or chuck 302 (and/or the laser 306) is operated so as to form the connecting aperture 332 at the terminal end and contiguous or continuous with the just-formed spiral void. Then at 362, the tube 170 is secured in place relative to the laser 306 and bushing 304 via for example a selectively actuatable tube grip that can be incorporated into the bushing 304 or elsewhere in the machine 300, while the chuck 302 releases its grip on the tube 170 and retracts laterally away from the laser 306 and bushing 304 to the home position. Once in the home position, the chuck 302 grips the tube 170 once again and the actuatable tube grip releases the tube. At 364, the chuck 302 and/or laser 306 is operated to aim or align the laser at or with the aperture 332. Once the laser 306 is so aimed or aligned, the chuck or rotating tool can be operated again as in 356 to rotate and laterally advance the tube 170 relative to the laser 306. Thus the laser 306 begins to cut another spiral segment in the tube sidewall. Because of the initial positioning of the laser beam 308 in the aperture 332, the new spiral segment begins at the perimeter of the aperture and the new segment is contiguous or continuous with the aperture 332 and the previous segment. As indicated at 368, acts 358-366 can now be repeated until the desired number of spiral segments and connecting apertures 332 are formed, over a desired cut length of the tube 170.

Figure 7:
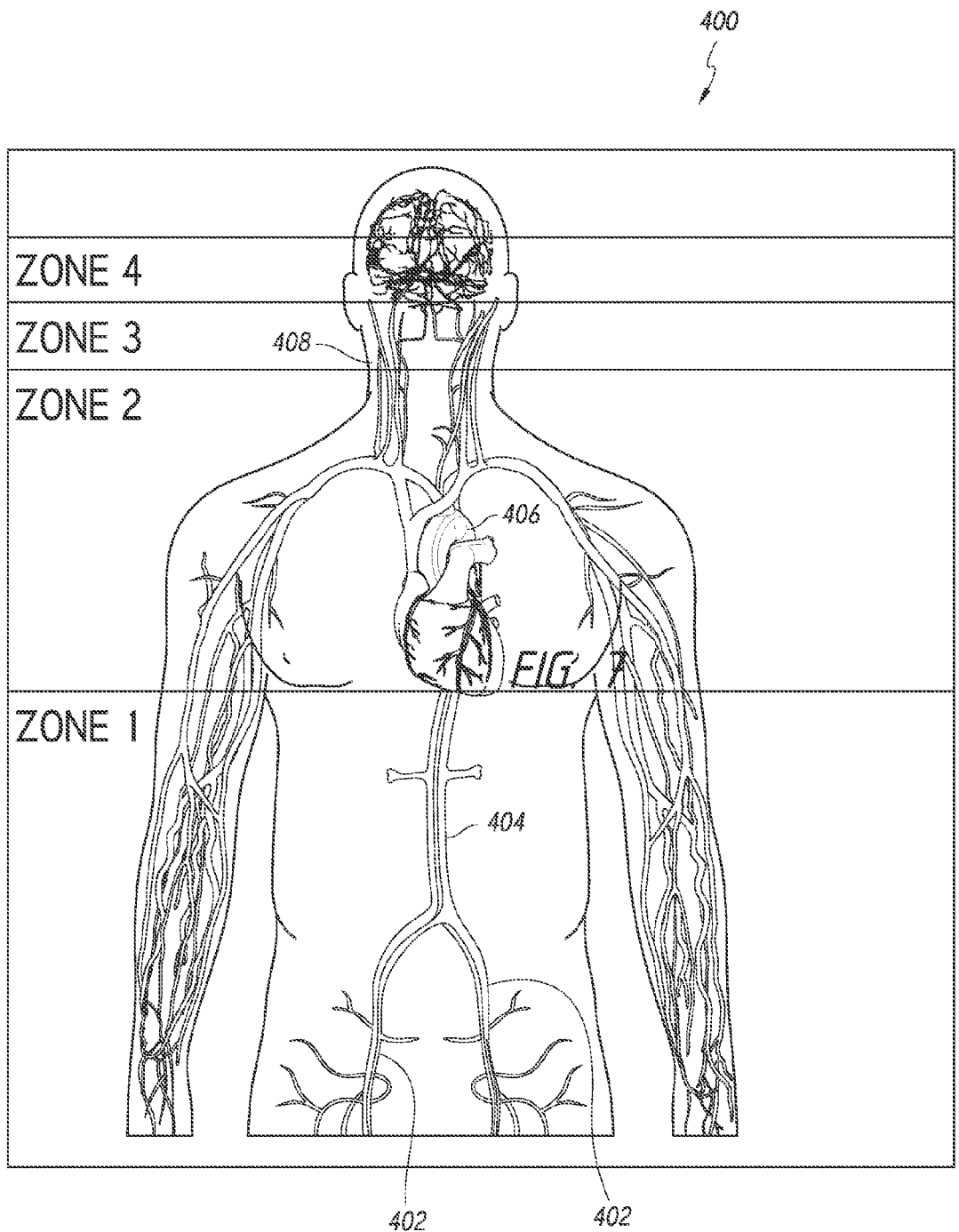
FIG. 7 is a schematic view of human vasculature, separated into representative zones, according to some embodiments.
Figure 8:
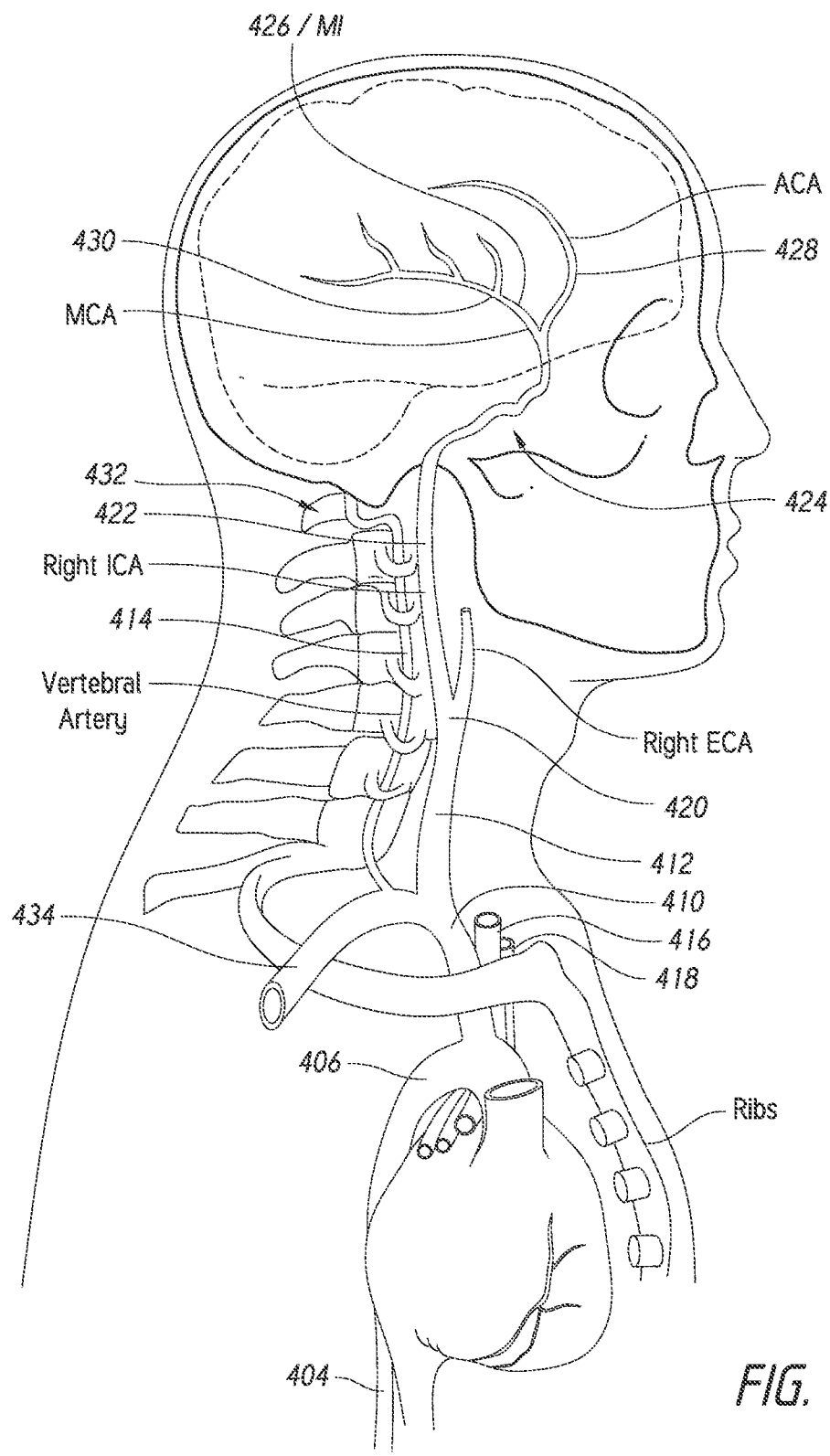
FIG. 8 is a schematic side view of human neurovasculature representative of some of the neurovasculature accessible with embodiments of the systems disclosed herein.

FIGS. 7 and 8 show a vascular access route 400 that can be employed in some embodiments of methods of using the intervention system 100, particularly in such methods of using the system 100 to deliver a medical device or the intervention member 200 to the neurovasculature. The route 400 can begin with percutaneous access into one of the femoral arteries 402 and then proceed to the abdominal aorta 404 and to the aortic arch 406. From the aortic arch 406 the route 400 can proceed up to and through the neck 408 through (A) the brachiocephalic artery 410 and (i) right common carotid artery 412 or (ii) right vertebral artery 414, or (B) the left common carotid artery 416, or (C) the left subclavian artery 418 and left vertebral artery (not shown). When the route 400 passes through the (right) common carotid artery 412 it can then proceed past the (right) carotid bifurcation 420 into the (right) internal carotid artery (ICA) 422. (The ICA commonly displays high tortuosity as shown at 424.) At the end of the ICA the route 400 can continue into one of the ICA's terminal branches, the middle cerebral artery (MCA) 426 or the anterior cerebral artery (ACA) 428. In the MCA 426 the route 400 can proceed through the M1 segment, to or beyond the M1 bifurcation 430.

When the route 400 passes through the (right) vertebral artery 414, it frequently encounters vertebral tortuosity such as shown at 432. From either vertebral artery, the route 400 can proceed through the basilar artery (not shown) to or past the basilar tip, posterior cerebral arteries (not shown), or posterior communicating arteries (not shown).

Instead of beginning at access via the femoral artery 402, the route 400 may begin at access via the left 418 or right 434 subclavian artery and proceed into the aortic arch 406, right common carotid artery 412 or right vertebral artery 414, and beyond as described above.

As seen in FIG. 7, the various embodiments of the vascular access route 400 may be divided into up to four zones: Zone 1, characterized by the relatively straight, large-diameter femoral artery 402 and abdominal aorta 404; Zone 2, including the sharply turning aortic arch 406 and its junctions with the arteries branching from the arch 406 toward the neck 408; Zone 3, with the common carotid and proximal vertebral arteries, and proximal ICA; and Zone 4, characterized by highly tortuous segments of the ICA 422 or vertebral artery 414, and/or smaller-diameter vessels that are frequently tortuous, such as the MCA 426 and leading up to or beyond the M1 bifurcation 430.

In some embodiments, the tube 170 can comprise a spiral-cut tube and the pitch of the spiral can vary along the overall length and/or cut length of the tube. The pitch can vary at a constant rate, or a non-constant rate. One or more segments of the cut length can have constant pitch, and these can be combined with one or more segments that have varying pitch. The tube 170 can incorporate spiral-cut and non-spiral-cut portions.

In some embodiments, the cut portion of the tube 170 can have two or more segments wherein the pitch is substantially constant (e.g., to impart mechanical properties suited to a desired one of the Zones indicated in FIG. 7) and these constant-pitch segments can be joined by segments in which the pitch varies. For example, a proximal segment may have a relatively high substantially constant pitch (in mm/rotation) to make the tube 170 relatively stiff in that segment, and a distal segment may have a relatively low substantially constant pitch (in mm/rotation) to make the tube 170 relatively flexible in that segment. These two segments may be joined by a varying-pitch segment in which the pitch is gradually reduced from that of the proximal segment to that of the distal segment. In this manner the tube 170 can incorporate a stiff proximal section for pushability and column strength, and a flexible distal section for navigability in tortuous vessels. The tube 170 can accommodate a relatively large change in pitch and stiffness between the proximal segment and the distal segment by making the change in pitch sufficiently gradual along the length of the varying-pitch segment. This can be done by incorporating a sufficient number of pitch transitions along the length of the varying-pitch segment. The number of pitch transitions per unit length of the tube can be considered a pitch transition density or PTD.

If, in a varying-pitch segment positioned between two segments that differ significantly in pitch or stiffness, the PTD is too low, the change in pitch/stiffness at any individual pitch transition will be relatively high; as a result the tube 170 may have an unduly high tendency to kink at such an individual pitch transition as the tube is advanced through a tortuous vessel and/or a high push force is exerted on the tube. In other words, if the tube incorporates an abrupt transition from a high-stiffness section to a low-stiffness section, the tube may be likely to kink at the transition point or segment when encountering a sharp turn in a vessel and/or application of a high push force.

Therefore, in order to accommodate in the tube 170 multiple segments that differ significantly in pitch/stiffness (and for example thereby tailor the mechanical properties of the tube segments to the various anatomical regions of the access route 400), without unduly increasing the tendency of the tube to kink, it can be useful to employ varying-pitch segments or transition zones that have a relatively high PTD or a relatively high overall number N of transitions. When the tube is forced to bend at or near a transition zone characterized by sufficiently high PTD and/or sufficiently high N, the bend becomes "spread" among the individual transitions in the transition zone, resulting in a gradual, arcing bend rather than a sudden, sharp kink.

Figure 9:
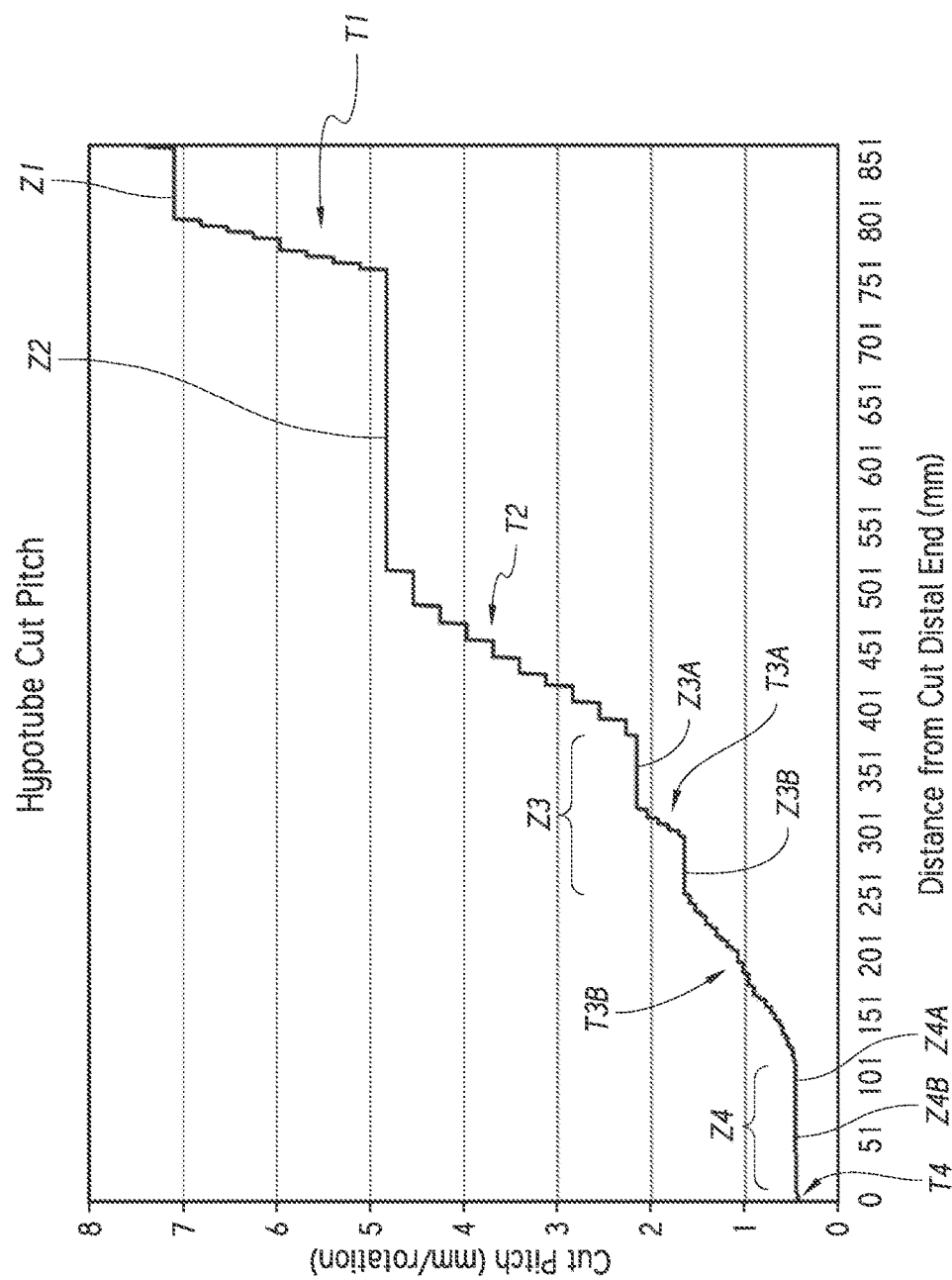
FIG. 9 is a graph illustrating the relationship between cut pitch and distance from a cut distal end of a helical cut in a tubular member, according to some embodiments.

FIG. 9 illustrates a varying pitch that may be used in some embodiments of the tube 170. The tube 170 may incorporate one or more multiple segments or flex zones of substantially or relatively constant pitch or stiffness, such as one, some or all of the zones Z1, Z2, Z3 (which can include two smaller zones Z3A, Z3B), and/or Z4 (which can include two smaller zones Z4A, Z4B). The flex zones can decrease in pitch/stiffness as the tube extends distally, e.g., with Z1>Z2>Z3>Z4 in pitch and/or stiffness. The zone Z1 can have a pitch and/or stiffness that is sufficiently flexible for navigation in Zone 1 of the access route 400 (FIG. 7), through the femoral artery 402 and abdominal aorta 404, while retaining pushability and column strength to move the distal portions of the manipulation member 160 through Zones 2, 3 and 4. The zone Z2 can have a pitch and/or stiffness that is sufficiently flexible for navigation in Zone 2 of the access route 400, particularly across the aortic arch and making a turn from the arch and extending into the one of the arteries leading to the neck (brachiocephalic 410, left common carotid 418 or left subclavian 418). The zone Z3 can have a pitch and/or stiffness that is sufficiently flexible for navigation in Zone 3 of the access route 400, particularly in the common carotid artery 412, or proximal portions of the internal carotid artery 422 or vertebral artery 414. The zone Z4 can have a pitch and/or stiffness that is sufficiently flexible for navigation in Zone 4 of the access route 400, particularly in the tortuous distal portions of the internal carotid artery 422 (such as the carotid siphon) and vertebral artery 414, and/or the middle cerebral artery 426 to the M1 bifurcation 430.

The flex zones Z1, Z2, Z3, Z4 can vary significantly relative to each other in pitch and/or stiffness in order to accommodate their respective target anatomies. For example, the zone Z4 can have a bending stiffness less than 5%, or less than 3%, or less than 2%, or less than 1% of the bending stiffness of the tube 170 when uncut. The zone Z3 can have a bending stiffness (A) greater than 8%, or greater than 10%, or greater than 12% of the bending stiffness of the tube 170 when uncut; and/or (B) less than 22%, or less than 20%, or less than 18%, or less than 17% of the bending stiffness of the tube 170 when uncut. The zone Z2 can have a bending stiffness (A) greater than 27%, or greater than 29%, or greater than 30% of the bending stiffness of the tube 170 when uncut; and/or (B) less than 36%, or less than 34%, or less than 33% of the bending stiffness of the tube 170 when uncut. The zone Z1 can have a bending stiffness (A) greater than 38%, or greater than 40%, or greater than 42% of the bending stiffness of the tube 170 when uncut; and/or (B) less than 50%, or less than 46%, or less than 44% of the bending stiffness of the tube 170 when uncut. The foregoing bending stiffness values and ranges can be implemented with reference to a tube 170 of any dimensions disclosed herein, including but not limited to a tube 170 having an outside diameter of 0.040" or less and/or a wall thickness of 0.010" or less. Such a tube may be constructed from materials including polymers, and metals including nitinol and stainless steels such as 304 or 304L stainless steel. One suitable tube 170 is constructed from 304L stainless steel with an outside diameter of 0.020" and a wall thickness of 0.003".

Instead of or in addition to the bending stiffnesses specified above, the zones Z1, Z2, Z3, and/or Z4 can have one, some or all of the following bending stiffnesses in Newtons times millimeters squared (N*mm^2): Z4, less than 12, less than 10, less than 8, or about 5; Z3B, 60-100, or 70-90, or about 80; Z3A, 90-130, 100-120, or about 110; Z2, 180-220, 190-210, or about 205; and/or Z1, greater than 250, greater than 270, or about 280, or 250-310, or 270-290. The uncut tube 170 can have a stiffness of 600-700, 625-675, or about 650. The foregoing bending stiffness values and ranges can optionally be normalized (to account for any differences in measuring equipment) with reference to a value of 340 N*mm^2 for 0.017" diameter solid wire made from 304 stainless steel.

One, some or all of transition zones T1, T2, T3A, and/or T3B can optionally be provided to incorporate these differences in pitch/stiffness while minimizing any resulting tendency of the tube to kink between the flex zones. The transition zones T1, T2, T3A and/or T3B can have relatively high PTD or N, as discussed above. For example, the transition zone T1 can have a PTD greater than 1.0 transitions per centimeter (T/cm), or of 2.0 T/cm or greater, or of about 2.0 T/cm; the transition zone T2 can have a PTD greater than 0.5 T/cm, or of 0.74 T/cm or greater, or of about 0.74 T/cm; the transition zone T3A can have a PTD greater than 1.5 T/cm, or of 2.2 T/cm or greater, or of about 2.2 T/cm; the transition zone T3B can have a PTD greater than 1.0 T/cm, or of 1.8 T/cm or greater, or of about 1.8 T/cm; and the transition zone T4 can have a PTD greater than 6.0 T/cm, or of 8.9 T/cm or greater, or of about 8.9 T/cm.

The transition zone T3B can provide a transition in flexibility from the relatively soft zone Z4, which can have a bending stiffness (such as any of those discussed above for Z4) suitable for navigating the distal ICA and M1 segment of the MCA, up to the stiffer zone Z3. Along the transition zone T3B, the pitch can increase significantly from the pitch employed in the zone Z4, by over 150%, over 200%, over 250%, or about 254%, to the pitch employed in zone Z3. The transition zone T3B can comprise a number of individual pitch transitions, such that the average overall percent increase in pitch achieved per individual transition is 15% or less, or 12% or less, or 11% or less, or 10.5% or less, or about 10.1%. (Such an average is computed by dividing the total percent increase in pitch achieved in the transition zone by the total number of transitions in the zone.) Instead of or in addition to any of these averages, the transition zone T3B can achieve a reduction in stiffness of greater than 75%, or greater than 85%, or greater than 90%, or about 94.5%, from the zone Z3 (particularly Z3B) to the zone Z4.

The transition zone T2 can provide a transition in flexibility from the zone Z3, which can have a bending stiffness (such as any of those discussed above for Z3) suitable for navigating the common carotid artery, proximal internal carotid artery, and/or proximal vertebral artery, to the stiffer zone Z2 which can have a stiffness (such as any of those discussed above for Z2) suited to crossing the aortic arch and/or extending into one of the arteries leading from the arch toward the neck. Along the transition zone T2, the pitch can increase significantly from the pitch employed in the zone Z3, by over 80%, over 100%, over 120%, or about 125%, to the pitch employed in zone Z2. The transition zone T2 can comprise a number of individual pitch transitions, such that the average overall percent increase in pitch achieved per individual transition is 20% or less, or 15% or less, or 13% or less, or about 12.5%. (Such an average is computed by dividing the total percent increase in pitch achieved in the transition zone by the total number of transitions in the zone.) Instead of or in addition to any of these averages, the transition zone T2 can achieve a reduction in stiffness of greater than 35%, or greater than 40%, or greater than 45%, or about 47%, from the zone Z2 to the zone Z3.

The transition zone T1 can provide a transition in flexibility from the zone Z2, to the stiffer zone Z1 which can have a stiffness (such as any of those discussed above for Z1) suited to passing through the femoral artery and abdominal aorta, and providing pushability for the more distal portions of the manipulation member 160. Along the transition zone T1, the pitch can increase significantly from the pitch employed in the zone Z2, by over 35%, over 40%, or about 45%, to the pitch employed in zone Z1. The transition zone T1 can comprise a number of individual pitch transitions, such that the average overall percent increase in pitch achieved per individual transition is 10% or less, or 8% or less, or 6% or less, or about 5.6%. (Such an average is computed by dividing the total percent increase in pitch achieved in the transition zone by the total number of transitions in the zone.) Instead of or in addition to any of these averages, the transition zone T1 can achieve a reduction in stiffness of greater than 15%, or greater than 20%, or greater than 25%, or about 27%, from the zone Z1 to the zone Z2.

Some, one or all flex zones Z1, Z2, Z3, Z4 can have a length greater than 30 mm, or greater than 40 mm. For example, the zone Z4 can have a length of 60 mm or more, or 80 mm or more, or 80-120 mm, or about 100 mm. The zone Z3B can have a length of 40-60 mm, or about 50 mm and the zone Z3A can have a length of 50-70 mm, or about 60 mm. The zone Z2 can have a length greater than 200 mm, or 200-300 mm, or 225-275 mm, or about 250 mm. The zone Z1 can have a length of 50-70 mm, or about 60 mm.

Instead of or in addition to any one or combination of the lengths specified above, the zones can be situated along the tube 170 with their respective distal ends located at the following distances from the distal end of the tube, or from the proximal end of the intervention member 200: Z4, 8-12 mm, or about 10 mm; Z3B, 225-275 mm, or 240-260 mm, or about 250 mm; Z3A, 300-340 mm, or 310-330 mm, or about 320 mm; Z2, 480-540 mm, 490-530 mm, or about 515 mm; and/or Z1, 780-820 mm, or 790-810 mm, or about 800 mm. By employing these locations along the tube, the zones Z1, Z2, Z3 and/or Z4 can be configured to occupy the anatomical regions described herein as corresponding to such region(s) when the distal end of zone Z4 or the intermediate region 166 is located within the M1 segment of the MCA.

The tube 170 can optionally include a transition zone T4 at the distal end of the cut length, e.g., distal of and adjacent to the zone Z4. The transition zone T4 can be configured to serve a "steering" function to point the tube 170 in the direction of travel of the distal portions of the manipulation member 160 (e.g., distal wire 172) as those distal portions navigate turns within the vasculature. Accordingly the zone T4 can have a relatively high PTD (e.g., over 5 T/cm, over 7 T/cm, or about 9 T/cm), a relatively short length (e.g., less than 15 mm, or less than 12 mm, or 8-10 mm, or about 9 mm), and/or an average stiffness less than the stiffness of the zone Z4 (e.g., a stiffness that decreases from that of zone Z4 as zone T4 extends distally).

Numerous parameters for various aspects of a spiral cut of the tube 170 are specified above. The scope of the present disclosure includes any single one or any combination of any number of the specified parameters. No one parameter, and no one value of any such parameter, should be regarded as essential.

Information regarding additional embodiments of the intervention system 100, and additional details, components and methods that can optionally be used or implemented in or with the embodiments of the system 100 described herein, can be found in U.S. patent application Ser. No. 14/040,463, filed on Sep. 27, 2013, and/or U.S. patent application Ser. No. 13/664,547, filed on Oct. 31, 2012, the entirety of each of which is hereby incorporated by reference herein. The intervention system 100 and methods disclosed herein can optionally be similar to any of the systems or methods disclosed in the above-incorporated applications.

Intervention Members

Figure 10:
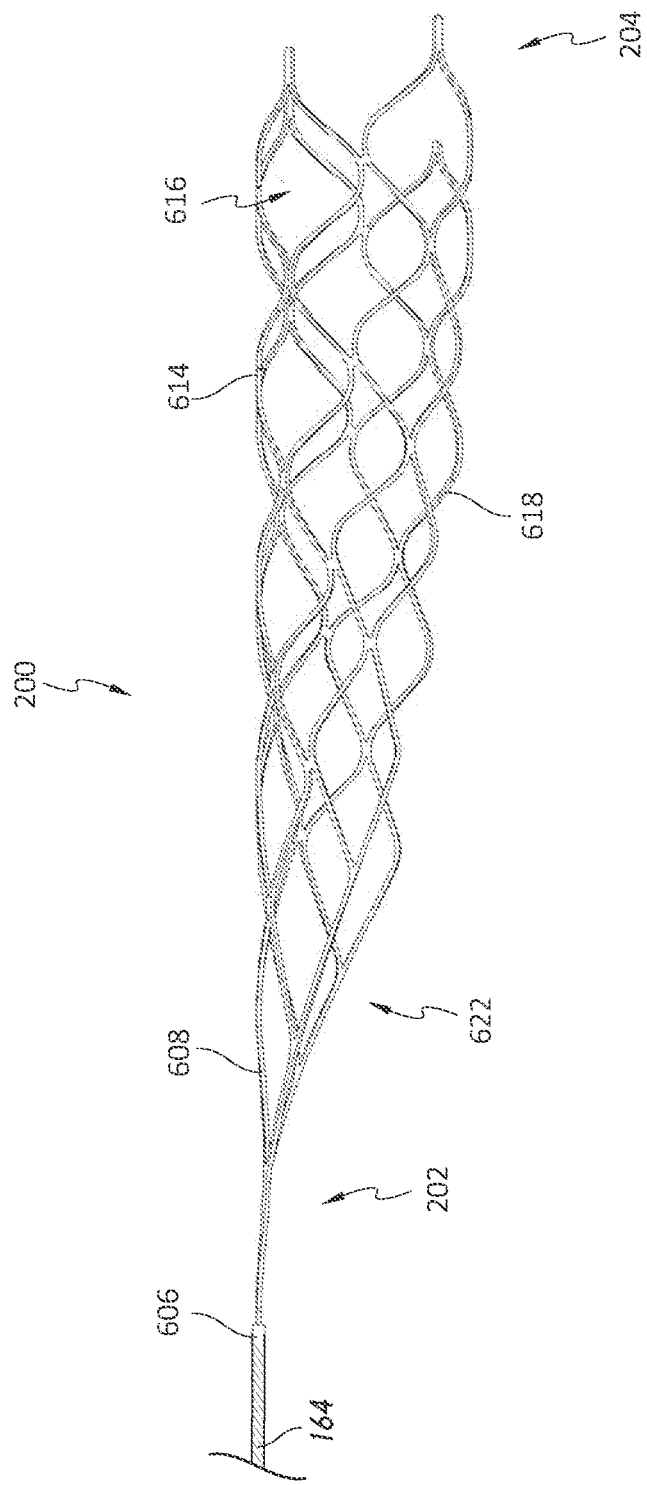
FIG. 10 illustrates a device, including an intervention member, for blood flow restoration, thrombus removal, or both, according to some embodiments.

FIG. 10 depicts an embodiment of the intervention member 200, according to some embodiments. In some embodiments, as discussed above, the proximal end portion 202 of the intervention member 200 and a distal end portion (e.g., a distal end of the wire 172) of the manipulation member 160 can be joined at a connection 606. The intervention member 200 and the manipulation member 160 can be substantially permanently attached together at the connection 606. That is, the intervention member 200 and the manipulation member 160 can be attached together in a manner that, under the expected use conditions of the assembly 600, the endovascular device and the manipulation member would not become unintentionally separated from one another.

Depending on the procedure and intended use of the intervention system 100, it optionally may be advantageous to have a connection mechanism that permits intentional release of the intervention member 200. For example, during a blood flow restoration procedure, it may prove difficult and/or dangerous to fully retrieve a thrombus due to a complicated vasculature or the risk of damaging a lumen wall. Leaving the intervention member 200 inside the patient may prove to be the only option available to a surgeon or other medical personnel, or it may be a goal of the procedure, such as when the intervention member 200 is deployed across an aneurysm (e.g., as an aneurysm bridge to retain coils or other materials in an aneurysm). In other circumstances the intervention member 200 may include drug-eluting capabilities, and/or may be coated with a particular type of drug that facilitates thrombus dissolution. It may be advantageous in such circumstances to release the intervention member 200 and allow the intervention member 200 to anchor the thrombus against the lumen wall while the thrombus is dissolved by the drug. In some embodiments, the intervention member 200 can comprise a portion, located proximally or distally of the connection 606, that is configured for selective detachment of the endovascular device 602 from the manipulation member 160. For example, such a portion can comprise an electrolytically severable segment of the manipulation member. In some embodiments, the intervention member 200 can be devoid of any feature that would permit selective detachment of the intervention member 200 from the manipulation member 160.

Further details regarding connections that can be employed between the intervention member 200 and the manipulation member 160 disclosed in U.S. Patent Publication No. 2014/0194919, published on Jul. 10, 2014; U.S. Patent Publication No. 2014/0194911, published on Jul. 20, 2014; U.S. patent application Ser. No. 14/026,302, filed on Sep. 13, 2013; and U.S. patent application Ser. No. 13/834, 945, filed on Mar. 15, 2013; the entirety of each of which is hereby incorporated by reference herein.

Figure 11:
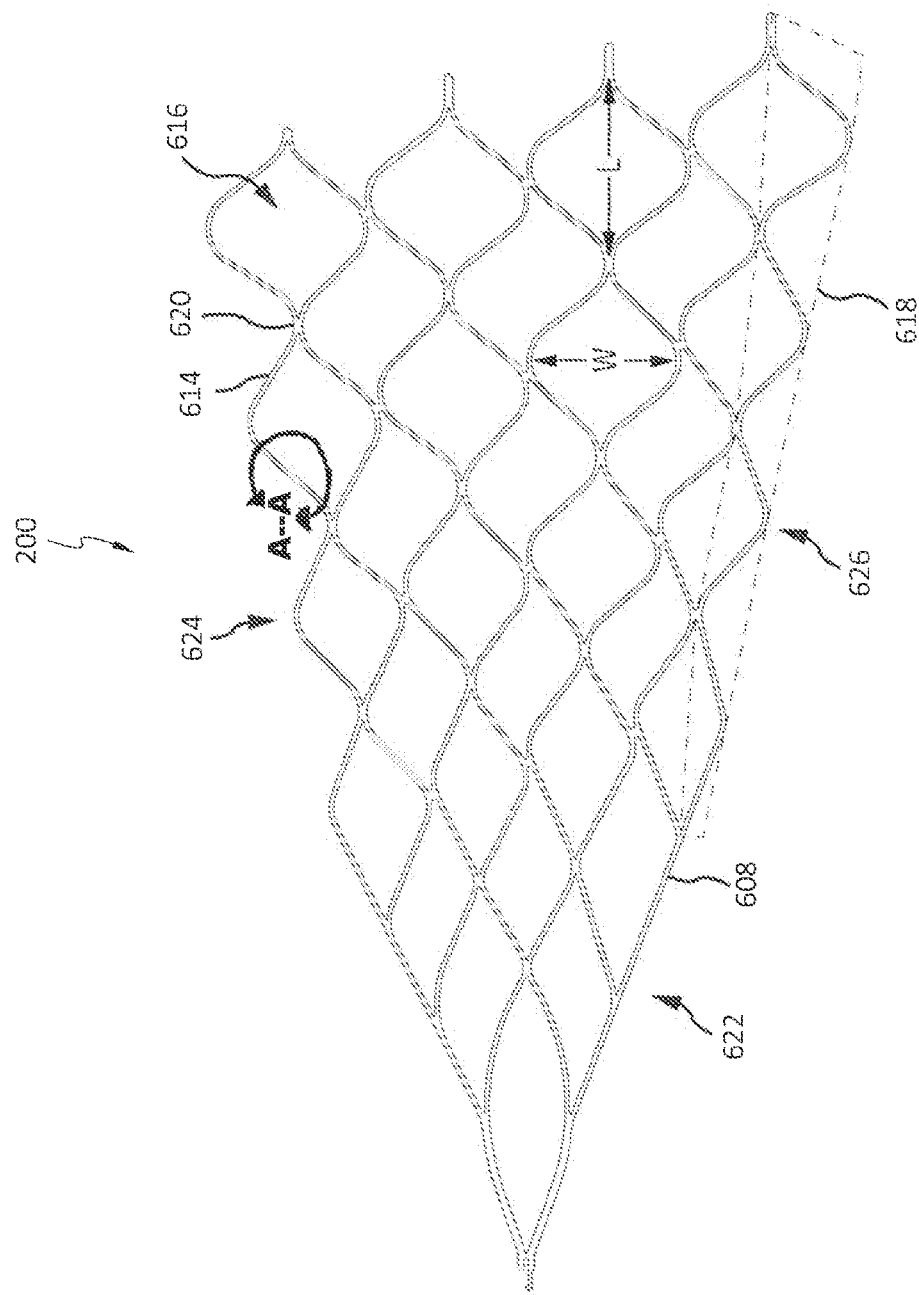
FIG. 11 illustrates an intervention member in an unrolled state, according to some embodiments.

FIG. 11 is a plan view showing an embodiment of the intervention member 200 in an unrolled state to facilitate description and understanding. As illustrated in FIG. 10, the intervention member 200 can have a tubular or generally cylindrical shape in absence of external forces, in some embodiments. The intervention member 200 can be self-expanding, e.g., by super-elasticity or shape memory, or expandable in response to forces applied on the intervention member 200, e.g., by a balloon.

As illustrated in FIGS. 10 and 11, the intervention member 200 can comprise a frame 608 having a proximal end portion 202 and a distal end portion 204. The frame can optionally comprise a plurality of struts 614. The struts 614 can optionally be configured to define a plurality of cells 616 and/or form a mesh. Groups of longitudinally and serially interconnected struts 614 can form undulating members 618 that extend in a generally longitudinal direction. The struts 614 can be connected to each other by joints 620. While the struts are shown having a particular undulating or sinuous configurations, in some embodiments the struts can have other configurations. The frame can have a generally tubular or generally cylindrical shape with one or both of the proximal end portion 202 and the distal end portion 204 being open.

As illustrated in FIGS. 10 and 11, a proximal portion 622 of the intervention member 200 can be tapered toward the proximal end portion 202. In some embodiments, the taper of the proximal portion can advantageously facilitate retraction and repositioning of the intervention member 200. In some embodiments, the tapered proximal portion can also be designed to generally not contact the vessel wall during a blood flow restoration procedure, and to generally not interfere with the flow of blood within a vessel.

Individual cells of the proximal portion 622 can have different sizes than individual cells located distal to the tapered proximal portion. For example, in some embodiments, the proximal portion 622 can have individual cells that have a size larger than that of the individual cells located distal to the tapered proximal portion. The proximal portion 622 can taper gradually towards the connection 606.

The taper of proximal portion 622 can be at various angles relative to the manipulation member 160. For example, in some embodiments, the taper can have an angle of approximately 45 degrees relative to the manipulation member, though other angles are also possible.

The intervention member 200 can comprise a first edge 624 and a second edge 626. The first edge 624 and second edge 626 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 624, 626 can be curved, straight, or a combination thereof along the tapered proximal portion 622.

The various embodiments of the intervention member 200 that are depicted or described herein provide one type of endovascular device or engagement member that may be employed as part of the intervention system 100, for example coupled to a distal end or portion of the manipulation member 160, for functions such as removal of a clot, thrombus, or other obstructions from the body. The engagement member can be expandable (either self-expandable or not), or non-expandable. The engagement member can be generally tubular (as in the depicted intervention member 200 in FIG. 10) in its deployed state, or it can have other forms when deployed. The engagement member can optionally form a mesh (as in the depicted intervention member 200 in FIG. 10), or it can have other structural configurations. The engagement member, when deployed, can form a body that extends along a central longitudinal axis that can be generally aligned or coincident with a central longitudinal axis of the manipulation member 160, and/or with a central longitudinal axis of the vessel in which the engagement member is deployed. The engagement member body can form an outer surface having (a) an outward-facing portion that faces radially outward, away from any one or more of the central longitudinal axes specified above, (b) an inward-facing portion that faces radially inward, toward any one or more of the central longitudinal axes specified above, and/or (c) a laterally-facing portion that faces in a direction generally parallel to any one or more of the central longitudinal axes specified above. Therefore, as discussed in U.S. patent application Ser. No. 14/541,094, filed on Nov. 13, 2014, the entirety of which is hereby expressly incorporated herein by reference, the presence or disposition of metals that can provide a galvanic effect (e.g., a first metal and a second metal, or an anodic metal and a cathodic metal), and various embodiments, configurations and alternatives for implementing such concepts, apply to the engagement member as well, and accordingly such a galvanic effect can be provided in or on the engagement member.

The intervention member 200 can be curled, rolled, or otherwise formed such that first edge 624 and second edge 626 overlap one another when the intervention member 200 is in a volume-reduced form. In a volume-reduced form, the frame 602 of the intervention member 200 can overlap to facilitate introduction of the intervention member 200 into and through the catheter 607. In some embodiments, the intervention member 200 is circumferentially continuous (e.g., forming a continuous cylindrical shape), lacking first and second edges 624, 626 and having no overlap or gap in a volume-reduced form and expanded form. Regardless of whether the intervention member 200 is circumferentially continuous, the intervention member 200 can have a central longitudinal axis both while in a volume-reduce form and when fully or partially expanded. In some embodiments, the intervention member 200 can be self-expandable, and can expand toward a fully expanded configuration upon release from the catheter 607. Upon expansion, the intervention member 200 can expand towards an inner wall of a vessel, towards a thrombus occluding the inner wall of a vessel, or both.

The extent of any overlap of the frame 608 can depend upon a degree of the frame's expansion. Expansion within a vessel can be limited, at least in part, by the vessel's size, and the amount and the properties of any thrombus present. For example, a greater overlap of the edges 624, 626 can occur in narrower vessels, whereas in wider vessels the overlap can be smaller, or even an "underlap" may occur, in which case the edges 22 and 24 are separated by an open gap or space within the vessel.

In some embodiments, the intervention member 200 can experience various degrees of overlap in a volume-reduced form, forming zones of overlap 628. The intervention member 200 can assume various diameters $\Delta_1$, $\Delta_2$, etc., depending on the degree of the overlap (e.g., represented by angle $\alpha_1$, $\alpha_2$, etc.). Overlap zones can vary in size and configuration depending on the vessel size. When inside a vessel, the overlap zone of the intervention member 200 can advantageously provide grip and/or retaining ability with respect to a thrombus. For example, when the intervention member 200 expands against a thrombus, the individual struts 614 and individual cells 616 of the overlap zone can embed into and grip, or retain, the thrombus. Alternatively, the intervention member 200 can be constructed without any overlap or edges 624, 626, e.g., as a continuous tube-like or cylindrical member.

The intervention member 200 can be manufactured in various lengths and relaxed-state diameters. In some embodiments, the intervention member 200 can have lengths, measured proximally to distally along the longitudinal axis, of 15 mm or less to 40 mm or more, though other ranges and sizes are also possible. The intervention member 200 can also have relaxed-state diameters, the diameters being measured when the intervention member 200 is fully free to expand, i.e., in absence of external forces. In some embodiments, the intervention member 200 can have a diameter of approximately 3 mm to 4 mm so as to be used in size 18 microcatheters (i.e., microcatheters with an inner diameter of approximately 0.21 inch). In some embodiments, the intervention member 200 can have a diameter of approximately 5 mm to 6 mm so as to be used in size 27 microcatheters (i.e., microcatheters with an inner diameter of approximately 0.027 inch). Other ranges and values are also possible.

Each cell 616 of the intervention member 200 can have a maximum length (labeled "L" in FIG. 11), as measured along a longitudinal axis of the intervention member 200, and a maximum width W, as measured along a direction generally perpendicular to the length (labeled "W" in FIG. 11). In some embodiments, cell size and dimensions can vary, as can the individual filament thicknesses and widths.

The location and longitudinal extent of thrombus engagement by a mechanical thrombus-retrieval device, e.g., the intervention member 200, can affect the likelihood of successfully capturing the engaged thrombus. Some embodiments of the subject technology increase the likelihood of successful thrombus capture and retrieval by increasing a longitudinal extent of substantially even thrombus engagement, distally shifting the region of increased thrombus engagement, or both. When a thrombus is primarily engaged along a portion of the thrombus near its proximal end, and particularly when a longitudinal extent of substantially even thrombus engagement is small, the thrombus may be more likely to fragment, become released from the retrieval device, or both.

In some embodiments, the intervention member 200 can be configured for substantially uniform or distally biased thrombus engagement, after expansion of the intervention member 200 into the thrombus, during retrieval of thrombus from a vessel by proximal retraction of the manipulation member 160. The thrombus can be generally soft, or malleable, or generally hard, or callous. For example, the intervention member 200 can have strut and cell dimensions that provide substantially uniform or distally biased thrombus engagement.

Figure 12:
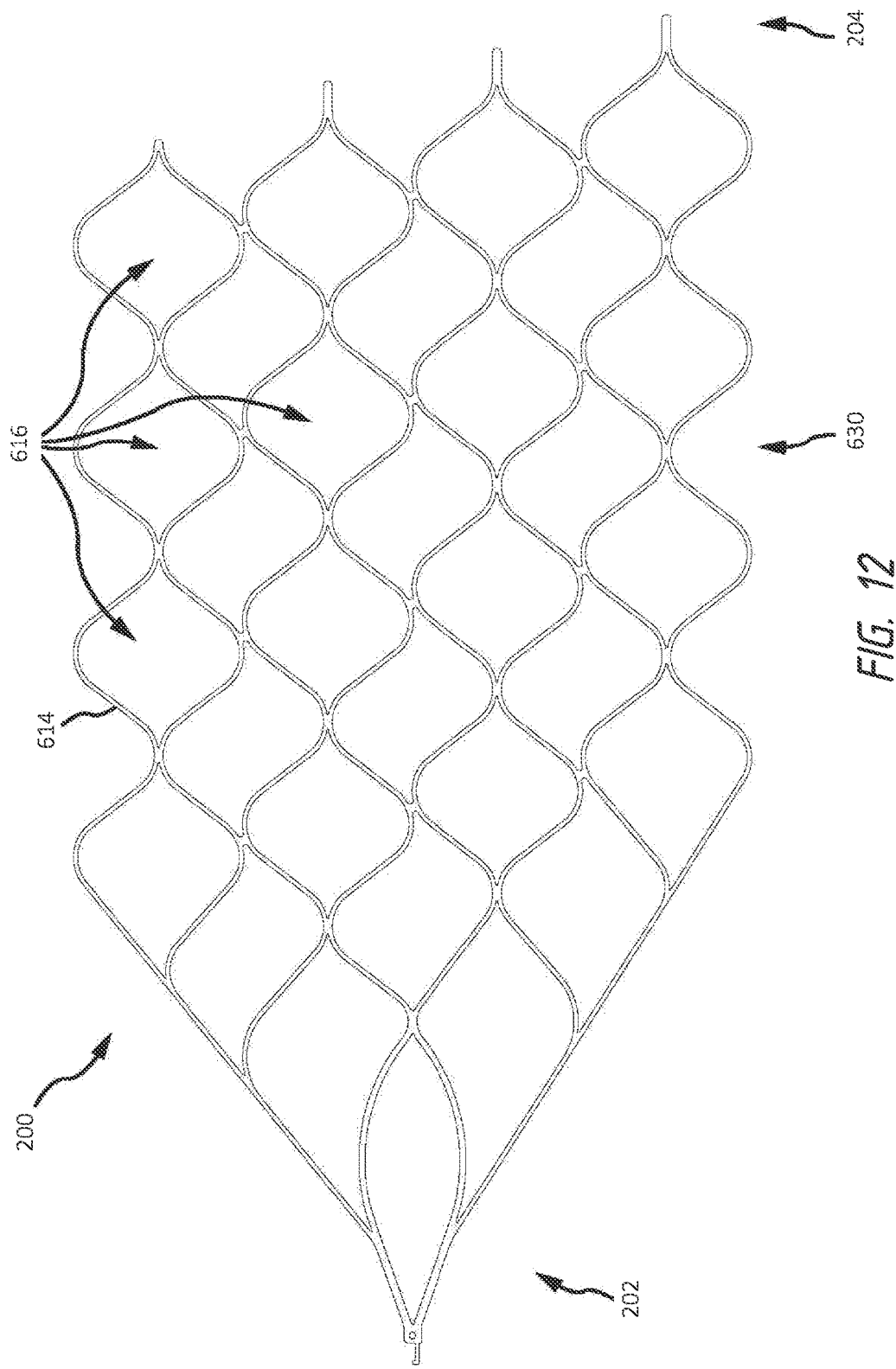
FIG. 12 illustrates an intervention member in an unrolled state, according to some embodiments.

FIG. 12 illustrates an intervention member 200 having a pattern 630 of cells 616 of substantially uniform dimensions and of struts 614 of substantially uniform dimensions. The pattern of cells and struts of FIG. 12 is substantially uniformly flexible or deformable. However, when the intervention member 200 of FIG. 12 is embedded in a thrombus and a proximally directed force is applied at a proximal end portion 202 of the intervention member 200, the cells of the intervention member 200 tend to collapse in width, and therefore engage a thrombus, more along a proximal portion of the substantially uniform pattern 630 than they do along a distal portion of the substantially uniform pattern 630. Such a proximally directed force may be considered to simulate the force exerted on the proximal end portion 202, via the manipulation member 160, during retrieval of the intervention member 200 in a procedure to remove, e.g., thrombus from a blood vessel.

Figure 13B:
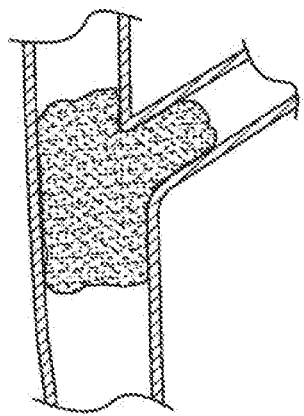
FIGS. 13A-13D schematically illustrate thrombi located in various vessel arrangements.
Figure 13D:
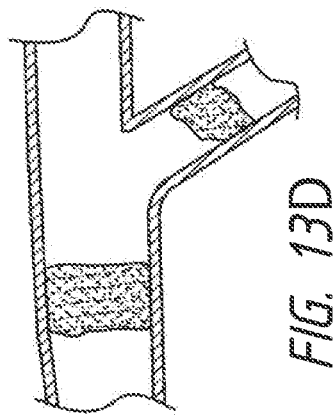
Figure 13A:
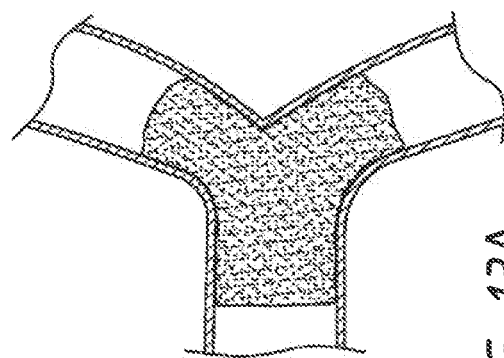
Figure 13C:
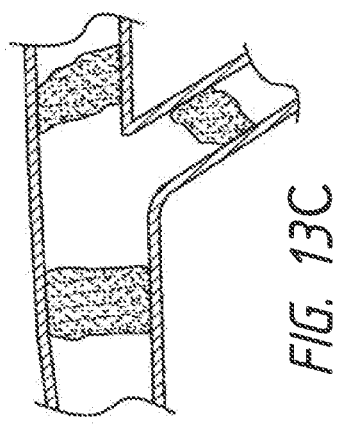

Referring to FIGS. 13A-13D, in some embodiments the intervention member 200 can be used as a flow restoration device and/or an implantable member (e.g., a stent) in a vessel, including at bifurcation, bi-vessel, and/or multi-vessel locations in mammalian vasculature, e.g., in the neurovasculature or in the peripheral vasculature. For example, and with reference to FIG. 13A, thrombi can be located at bifurcations in the neurovasculature such as the internal carotid artery and the anterior cerebral artery, or internal carotid artery and middle cerebral artery, or the basilar artery and the posterior cerebral artery. With reference to FIG. 13B, thrombi can also be located at two vessels (i.e., bi-vessels) as two separate clots in similar vessels. With reference to FIGS. 13C and 13D, thrombi can also be located at multi-vessels as one clot that is within multiple vessels or as multiple clots that are within multiple vessels. Vessels with such clots can be located, for example, at the intracranial internal carotid, anterior cerebral and middle cerebral arteries, and basilar artery and both posterior and cerebral arteries, or in the peripheral vasculature, such as the deep venous system of the legs when treating deep vein thrombosis.

Figure 14:
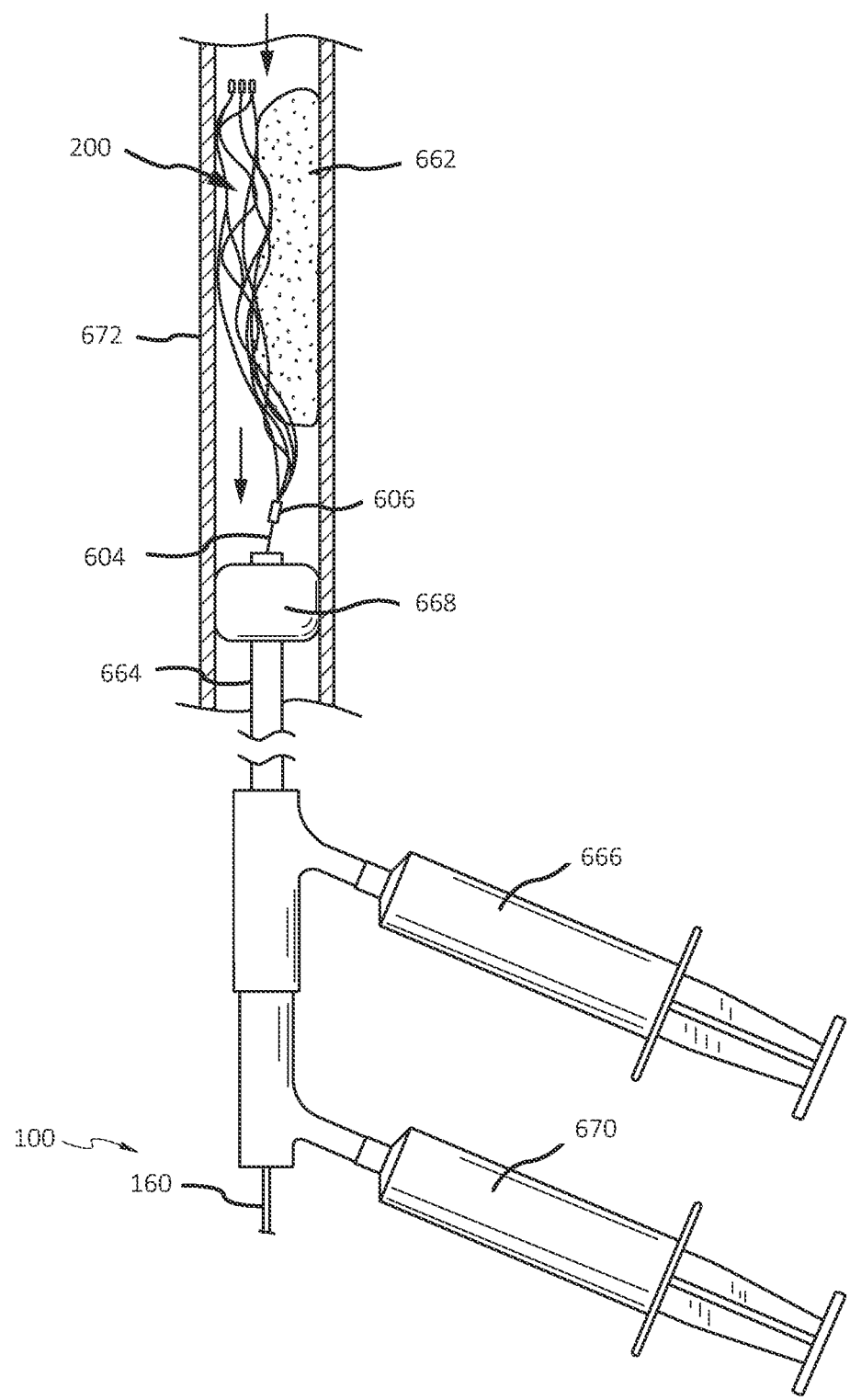
FIG. 14 schematically illustrates a system for blood flow restoration, thrombus removal, or both, according to some embodiments.

Referring to FIG. 14, the intervention system 100 can be used in a system with a balloon guide catheter 664, with a syringe 666 for expanding a balloon 668, a syringe 670 for aspiration, or both. Aspiration assistance can enable flow reversal through the intervention member 200 and thrombus 662. Inflation of the balloon 668 can impede or prevent flow proximally through the vessel from the balloon 668 towards the intervention member 200. As part of the retrieval procedure, continuous aspiration can be employed through the balloon guide catheter 664, with vigorous aspiration when the intervention member 200 is near a distal tip of the balloon guide catheter. The aspiration with flow reversal can help allow the distal vasculature to continue to have blood perfusing through the vessels during the retrieval process, and can inhibit the possibility of distal emboli. There can be an advantage to having blood flow across the intervention member 200 and thrombus 662 with the potential of natural lysing of blood and increased surface area for thrombus dissolving medicines, if they are provided. The aspiration with flow reversal can also assist in the thrombus retrieval process by aiding in the removal of the thrombus 662. The flow can be directed towards a lumen of the balloon guide catheter 664 due to the aspiration. The intervention member 200 and thrombus 662 can thus be assisted by the flow to enter the lumen of the balloon guide catheter 664. In some embodiments, if withdrawal into the balloon guide catheter 664 is difficult for any reason during aspiration, the balloon 668 can be deflated, and the balloon guide catheter 664, catheter 607, and intervention member 200 can be withdrawn simultaneously while maintaining aspiration.

Figure 15:
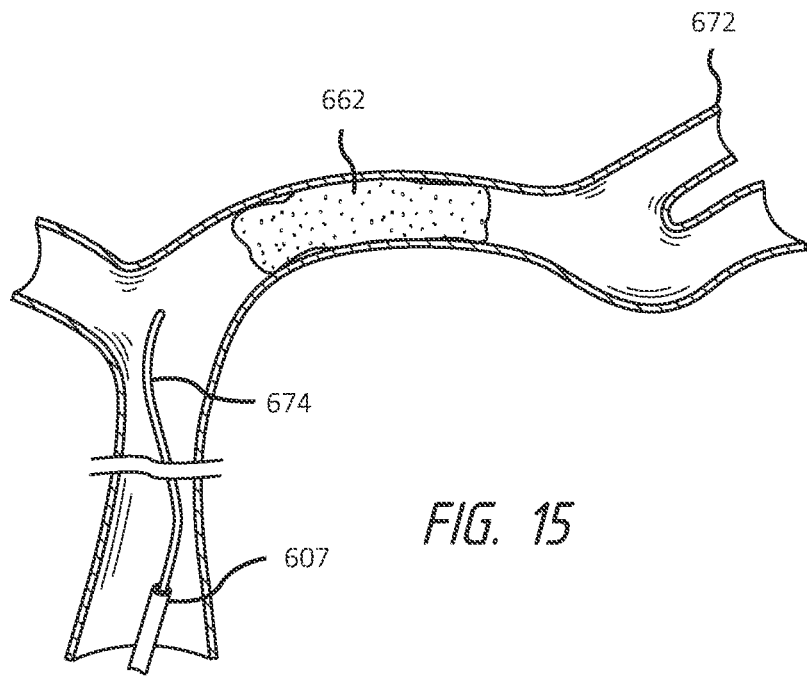
FIGS. 15-24 are cross-sectional views of a vessel and illustrate use of an intervention member, according to some embodiments.
Figure 16:
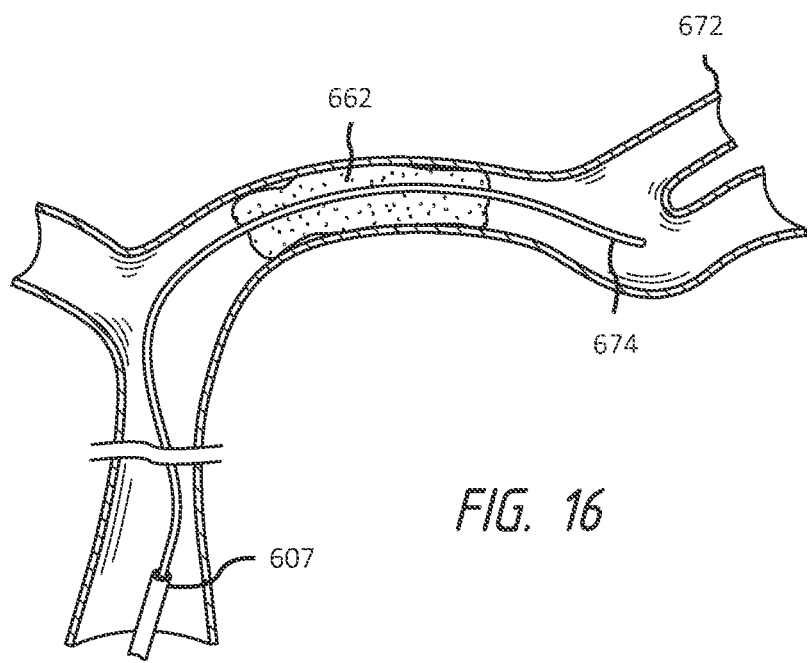
Figure 17:
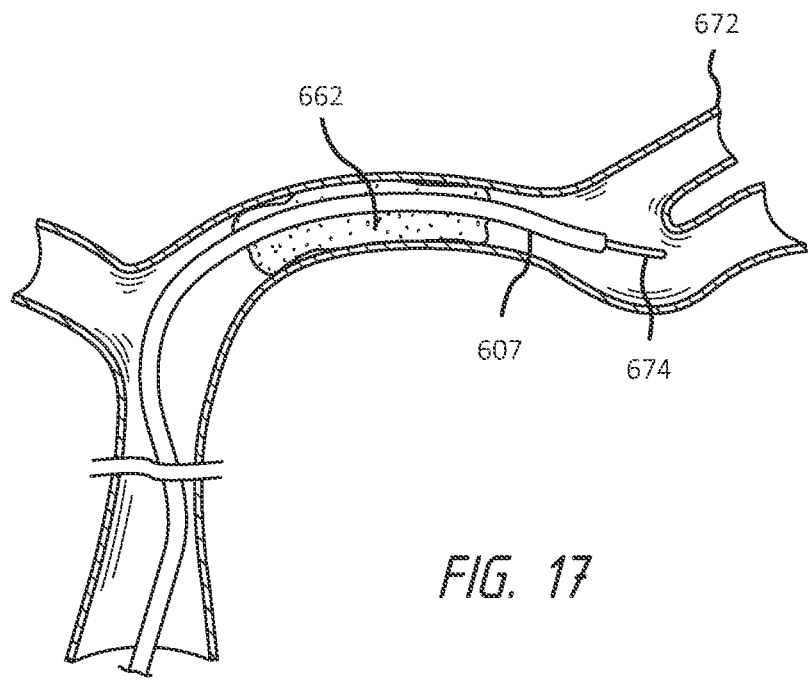

A technique for engaging and removing a thrombus 662 and restricting downstream travel of secondary emboli during thrombus retrieval will now be discussed with reference to FIGS. 15-24. This technique can be performed with any of the embodiments of the manipulation member 160 and intervention member 200 disclosed herein, including any intervention member disclosed herein. Referring to FIG. 15, the intervention system 100 may be inserted into an anatomical vessel 672 by first inserting a guide wire 674 into the anatomical vessel 672. The guide wire 674 is advanced through a guide catheter 664, which optionally includes a balloon near the guide catheter's distal end, and a catheter 607 to the treatment site, adjacent the thrombus 662. Referring to FIG. 16, the guide wire 674 is advanced distally through the thrombus 662. Once in position, the catheter 607 is advanced over the guide wire 674, through a distal end of the guide catheter, into the anatomical vessel 672. Referring to FIG. 17, the catheter 607 is advanced distally through the thrombus 662. The guide wire 674 is then withdrawn proximally.

Figure 18:
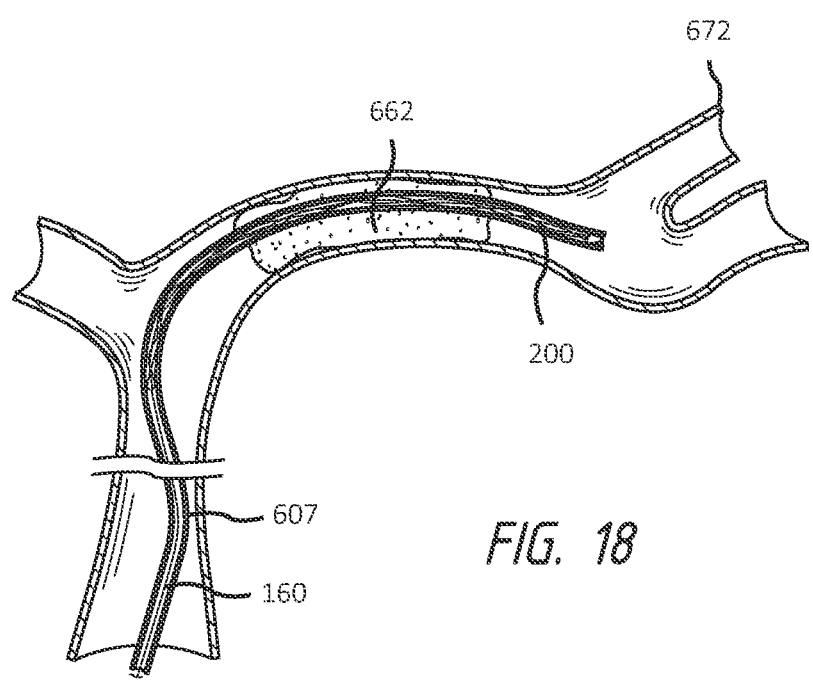

Referring to FIG. 18, the intervention member 200 is advanced through the catheter 607 such that the distal end portion of the intervention member 200 is disposed distal of the thrombus 662 in the anatomical vessel 672. The intervention member 200 is advanced through the catheter 607 by the manipulation member 160 coupled to the proximal end of the intervention member 200. The catheter 607 compresses the intervention member 200 and thus maintains the intervention member 200 in a compressed, volume-reduced configuration as the intervention member 200 is advanced to the treatment site.

In some embodiments, where the manipulation member 160 includes a tube 170 with transition zones T3B, T3A, T2, and/or T1, as discussed above with respect to FIGS. 2-9, advancing the manipulation member 160 (in this method or in any method of advancing the manipulation member 160 through a tortuous catheter) can comprise forming a rounded, arc-like and/or non-kinking bend in the tube 170 in one or more of such transition zones T3B, T3A, T2, and/or T1, e.g., between the portions of the tube longitudinally adjacent to the transition zone(s) being so bent. Further, in some embodiments, where the manipulation member 160 includes a tube 170 with flex zones Z4, Z3, Z2, and/or Z1, as discussed above with respect to FIGS. 2-9, advancing the manipulation member 160 (in this method or in any method of advancing the manipulation member 160 through a tortuous catheter) can further comprise any one or combination of the following: advancing zone Z4 into or through the cavernous ICA, the carotid siphon, the M1 segment of the MCA, and/or the M2 segment of the MCA; advancing zone Z3 into the proximal portion of the ICA, proximal of the cavernous ICA, and/or into or through the common carotid artery; advancing zone Z2 into or through the aortic arch, and/or into any of the arteries originating at the arch and leading toward the neck; and/or advancing zone Z1 into the femoral artery and/or the abdominal aorta. The respective flex zone(s) can occupy one, some or all of the foregoing anatomical regions while the intervention member 200 coupled to the manipulation member 160 and moved into the M1 or M2 regions of the MCA. Additionally, as the intervention member 200 moves closer to the distal end of the catheter, the user can observe a fluorosafe marker (when present) approaching the proximal end of the catheter and thereby recognize that the intervention member 200 is or will soon be close to exiting the distal end of the catheter, as discussed in U.S. patent application Ser. No. 14/040,463, filed on Sep. 27, 2013, the entirety of which is expressly incorporated herein by reference. Having recognized this, the user can activate fluoroscopic imaging to view the exit of the intervention member from the distal catheter end via such imaging, and then proceed to urge the manipulation member distally and thereby cause the intervention member to exit the distal end of the catheter.

Figure 19:
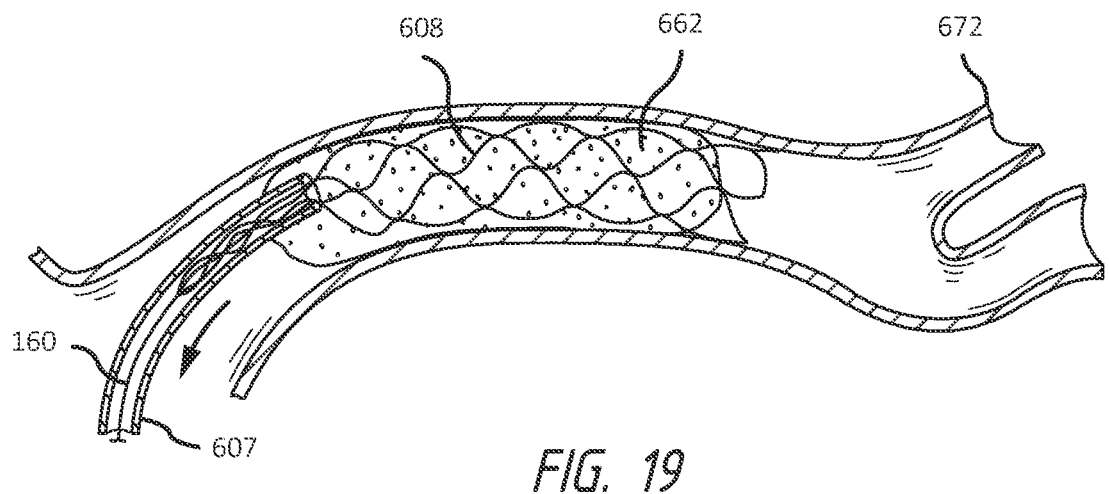
Figure 20:
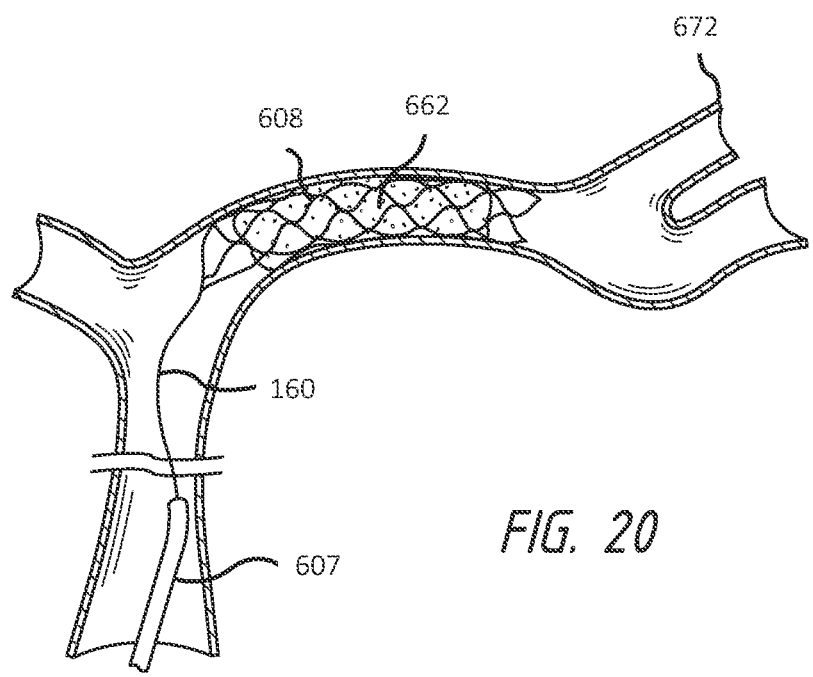

Referring to FIGS. 19 and 20, the catheter 607 is withdrawn proximally relative to the intervention member 200 to expose the intervention member 200. If the intervention member 200 is self-expanding, retraction of the catheter 607 can permit the intervention member 200 to expand. The frame 608 expands against a length of the thrombus 662 and engages the thrombus 662. As discussed above, the frame 608 is designed to engage and remove thrombi that are both generally soft, or malleable, or generally hard, or callous. A period of time can be allowed to pass to allow blood to reperfuse the downstream area, the intervention member 200 to penetrate the thrombus 662, or both.

In accordance with some embodiments of methods disclosed herein, when operating the intervention system 100, a clinician can check the initial partial expansion of the intervention member 200 and, if the initial placement is unsatisfactory or if the initial expansion of the intervention member 200 is unsatisfactory, the clinician can recapture, collapse, withdraw, or resheath the intervention member 200 into the catheter. After resheathing, the clinician can attempt to deploy the intervention member 200 again. Resheathing can also be performed, and the manipulation member 160 and the intervention member 200 removed from the patient entirely, if for example, the delivery and/or expansion of the intervention member 200 damages or reveals a defect in, or improper sizing of, the intervention member 200 or the intervention system 100. After an initial partial expansion of the intervention member 200, the depicted manipulation member 160 can optionally be entirely removed with the intervention member 200 from the catheter without need to remove the catheter from the blood vessel. In this manner, access to the treatment site in a blood vessel can be maintained via the catheter and, if desired, additional treatment can be performed using the catheter. In the present disclosure, numerous references are made to moving the catheter axially over the manipulation member 160 and/or the intervention member 200, and moving the manipulation member 160 and/or the intervention member 200 axially within the catheter. Except where specifically noted to the contrary, all such references to one form of this relative movement should be understood to include the other as an alternative.

Once the intervention member 200 has been expanded into the thrombus 662, the intervention member 200 can grip the thrombus, by virtue of its ability to mechanically interlock with the thrombus as well as its ability to electrically attract, adhere, and/or attach to the thrombus 662. The galvanic cell(s) and/or region(s) can begin a galvanic reaction before or after the intervention member 200 has been released from the catheter 607 into the anatomical vessel 672 (e.g., an intracranial vessel) and/or expanded into the thrombus 662, as discussed in U.S. patent application Ser. No. 14/541,094, filed on Nov. 13, 2014, the entirety of which is expressly incorporated herein by reference.

In some embodiments, at least a portion of the thrombus 662 is attracted, adhered, and/or attached to an inwardly facing surface of the intervention member 200. Blood constituents can be bound primarily or substantially only to an inwardly facing surface of the mesh in some embodiments.

Figure 21:
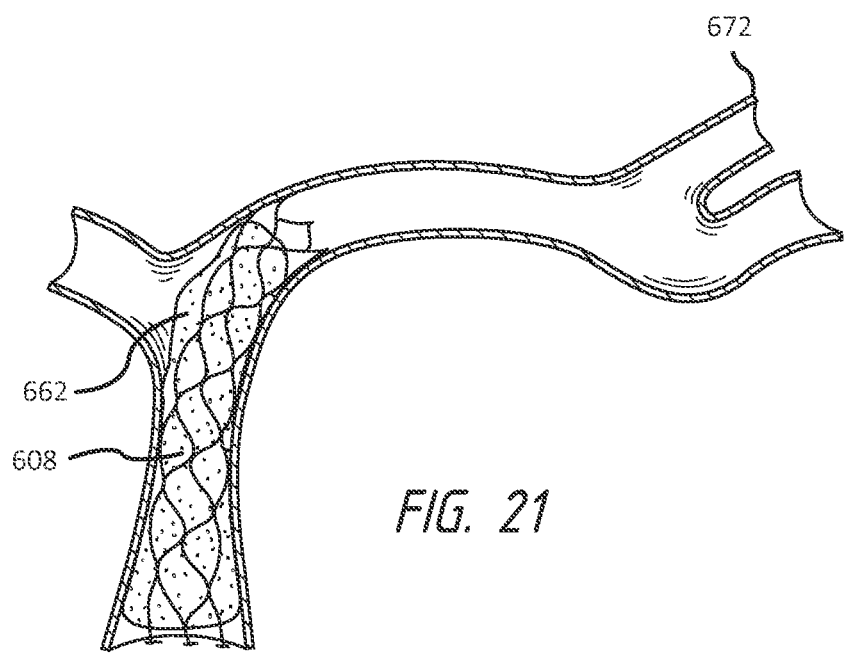
Figure 22:
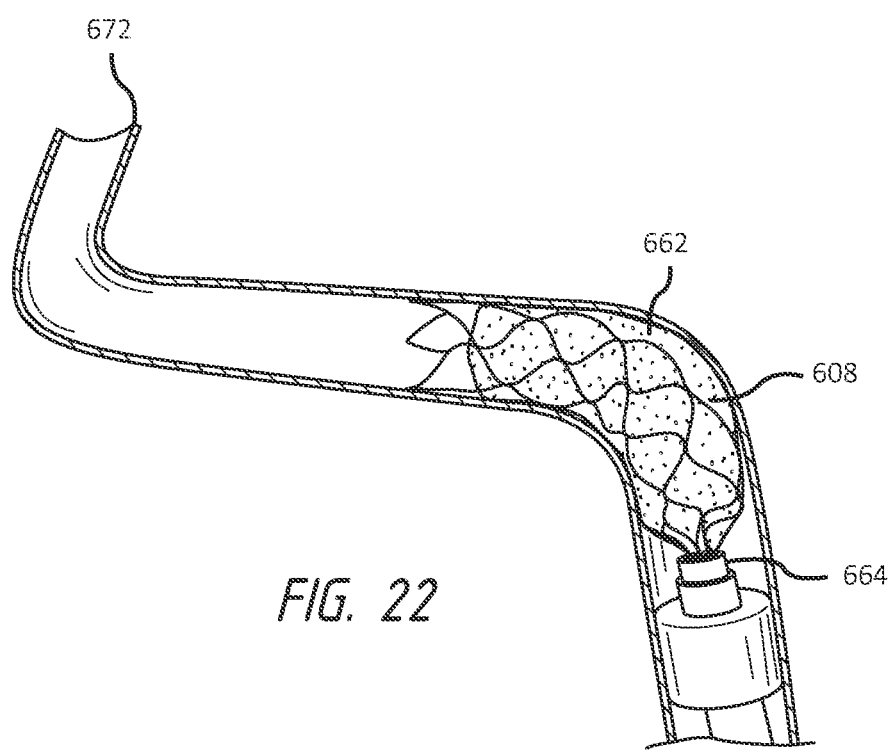
Figure 23:
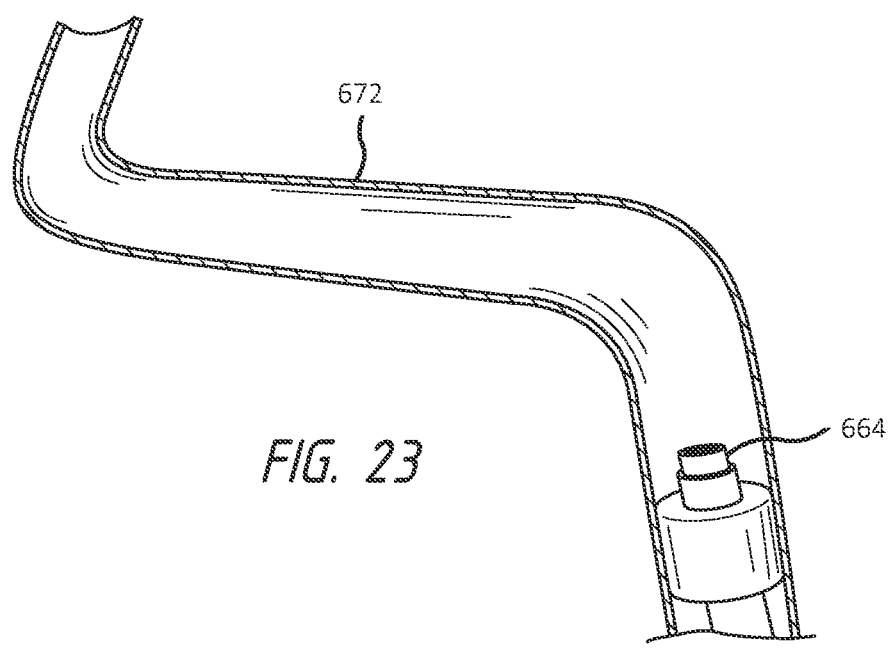

With reference to FIGS. 21-23, once the intervention member 200 has engaged and captured the thrombus 662, the thrombus 662 can be removed. For example, the intervention member 200 with the thrombus 662 gripped thereby, can be retracted (for example, along with the microcatheter 608) proximally toward the balloon guide catheter. During this retraction, the intervention member 200 can grip the thrombus 662 electrostatically, e.g., via galvanic cell(s) and/or region(s) of the intervention member 200. Accordingly, the intervention member 200 can maintain an enhanced or electrostatically-enhanced grip on the thrombus 662 during retraction. The intervention member 200 and thrombus therefore form a removable, integrated thrombus-device mass wherein the connection of the thrombus to the device is electrostatically enhanced, e.g., via galvanic cell(s) and/or region(s), as discussed in U.S. patent application Ser. No. 14/541,094, filed on Nov. 13, 2014, the entirety of which is expressly incorporated herein by reference.

Prior to retracting the intervention member 200 and thrombus 662, the catheter 607 or the guide catheter 664 can be manipulated. For example, the catheter 607 or the guide catheter 664 can be moved forward to a predetermined point relative to the intervention member 200. Use of markers along the catheter 607, or the guide catheter 664, and/or intervention member 200 can be used to determine the relative locations of the catheter 607, the guide catheter 664, and intervention member 200. Description of the use of such markers can be found, for example, in PCT Publication No. WO2009/105710, which is expressly incorporated herein by reference in its entirety.

Referring to FIGS. 21 and 22, the intervention member 200 is withdrawn proximally, along with the thrombus 662. Applying a proximally directed force to a proximal end of the frame 608 can collapse a distal end of the frame 608, prior to withdrawal of the intervention member 200 into the guide catheter 664. The distal end of the frame 608 can collapse to at least substantially the same extent, and optionally more than, a portion of the frame proximal of the distal end, as discussed above.

Referring to FIGS. 14, 22, and 23, in embodiments wherein the guide catheter 664 comprises a balloon 668, the balloon optionally can be inflated to occlude flow during retraction of the thrombus 662 toward the guide catheter. In some embodiments, an aspiration syringe 670 can be attached to the guide catheter 664, and aspiration can be applied to aid thrombus retrieval.

Figure 24:
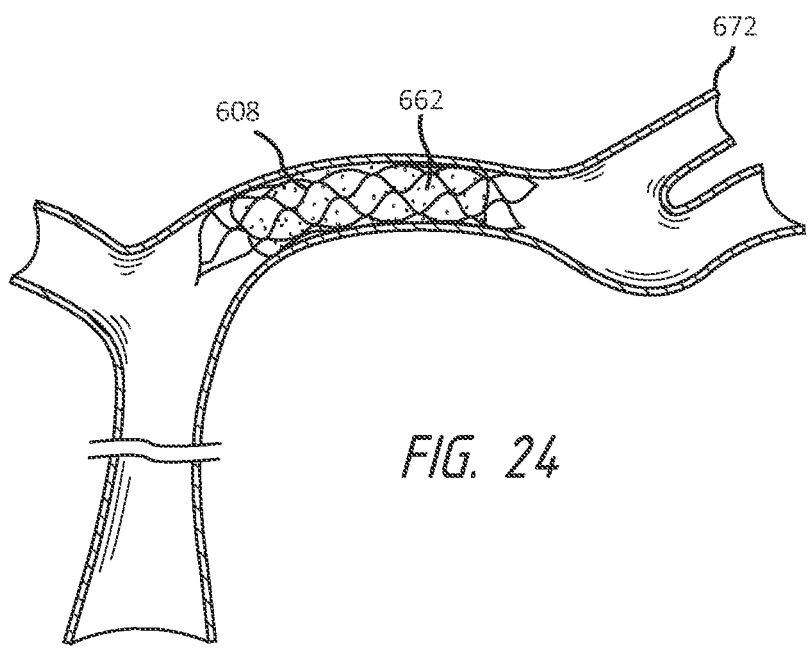

Referring to FIG. 23, the intervention member 200 is withdrawn proximally to the guide catheter 664. The guide catheter 664 causes the frame 608 to collapse, with the thrombus 662 engaged therein. The thrombus 662 is thus retrieved and removed from the anatomical vessel 672. Referring to FIG. 24, if retrieval of the intervention member 200 is determined to be undesirable, e.g., to avoid damaging the vessel 672, and the intervention member 200 is detachably connected to the manipulation member 160, the intervention member 200 can be detached from the manipulation member 160 and can remain in the vessel 672.

Additionally, while the intervention member 200 described above has been described in the context of use during a blood flow restoration procedure, the intervention member 200 can also, or alternatively, be used as an implantable member (e.g., a stent). For example, the intervention member 200 can be released through the connection 606 at a stenosis, aneurysm, or other appropriate location in a vessel. The intervention member 200 can expand and engage a vessel wall so as to hold the vessel wall open and/or act as an occluding member. While the filament thicknesses, widths, cell sizes, and forces described above can be optimized for an intervention member 200 for flow restoration, these values can also be optimized for an intervention member 200 for use as an implantable member. In some embodiments the same values can be used for both flow restoration and use as an implantable member.

Further, the intervention member 200 can also be used to engage with and retrieve one or more implants, stents, coils, or other structures within the vessel. The intervention member 200 can be actuated between a disengaged and an engaged configuration to engage one or more implants, stents, coils, or other structures. Moreover, the implant, stent, coil, or other structure can be captured or retrieved into the catheter, as discussed similarly herein regarding thrombus retrieval.

Further details regarding intervention members, the manufacture of intervention members, and use of intervention members are disclosed in U.S. Pat. No. 7,300,458, issued Nov. 27, 2007; U.S. Patent Application Publication No. 2011/0060212, published on Mar. 10, 2011; U.S. Patent Application Publication No. 2012/0083868, published on Apr. 5, 2012; U.S. Patent Application Publication No. 2011/0160763, published on Jun. 30, 2011; U.S. Patent Publication No. 2014/0194919, published on Jul. 10, 2014; and U.S. Patent Publication No. 2014/0194911, published on Jul. 20, 2014; and U.S. patent application Ser. No. 14/026,302, filed on Sep. 13, 2013; the entirety of each of which is hereby incorporated by reference herein.

Further Aspects of Some Embodiments

The apparatus and methods discussed herein are not limited to the deployment and use of a medical device or stent within the vascular system but may include any number of further treatment applications. Other treatment sites may include areas or regions of the body including any hollow anatomical structures.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A medical device comprising:
    a manipulation member comprising a tubular member having an elongate tubular body and a continuous helical cut extending along the body, the cut having an axial length of at least 50 cm, the cut comprising first and second helical slots joined by a connection aperture, wherein a pitch of the cut varies along the first and second helical slots; and
    an intervention member configured for mobilizing thrombus, the intervention member being coupled to a distal portion of the manipulation member and advanceable via the manipulation member,
    wherein a segment of the cut is configured such that the pitch of the cut changes in magnitude at both ends of the segment, by 0.2 mm/rotation or less.

2. The device of claim 1, wherein the segment is located 10 cm or more from an endpoint of the cut.

3. The device of claim 1, wherein the length of the segment is 5 mm or less.

4. The device of claim 1, wherein the intervention member comprises a mesh having a plurality of cells in a generally tubular configuration.

5. The device of claim 1, wherein the intervention member comprises an expandable body having a plurality of struts.

6. The device of claim 5, wherein the struts include radially peripherally located struts.

7. The device of claim 5, wherein the struts include radially transversely extending struts.

8. The device of claim 1, wherein the intervention member comprises at least one expandable wire.

9. The device of claim 1, wherein the intervention member comprises a longitudinally connected plurality of expandable bodies.

10. The device of claim 1, wherein the intervention member is substantially permanently coupled to the manipulation member.

11. The device of claim 1, wherein the intervention member is coupled to a distal tip of the manipulation member and extends distally from the distal tip.

12. The device of claim 1, wherein the intervention member comprises a thrombus removal device.

13. A vascular intervention system sized for insertion into a blood vessel, the system comprising a manipulation member and an intervention member coupled to the manipulation member, the manipulation member comprising a tube with a plurality of slots connected in an end-to-end manner to form a continuous helical void extending along a length of the tube, wherein adjoining slots intersect with a connection aperture extending through a wall of the tube and having a diameter greater than respective widths of the adjoining slots, the intervention member being configured for mobilizing thrombus, wherein a segment of the void is configured such that a pitch of the void changes in magnitude, at both ends of the segment, by 0.2 mm/rotation or less.

14. The system of claim 13, wherein the pitch of the void changes in magnitude at both ends of the segment, by 0.1 mm/rotation or less.

15. The system of claim 13, wherein the length of the segment is 5 mm or less.

16. The system of claim 13, wherein the segment is located 10 cm or more from an endpoint of the void.

17. The system of claim 13, wherein the segment is a first segment, and the pitch of the void changes in magnitude from the first segment to an adjacent second segment by 0.1 mm/rotation or less.

18. The system of claim 13, wherein the intervention member comprises a mesh having a plurality of cells in a generally tubular configuration.

19. The system of claim 13, wherein the intervention member comprises an expandable body having a plurality of struts.

20. The system of claim 19, wherein the struts include radially peripherally located struts.

21. The system of claim 19, wherein the struts include radially transversely extending struts.

22. The system of claim 13, wherein the intervention member comprises at least one expandable wire.

23. The system of claim 13, wherein the intervention member comprises a longitudinally connected plurality of expandable bodies.

24. The system of claim 13, wherein the intervention member is substantially permanently coupled to the manipulation member.

25. The system of claim 13, wherein the intervention member is coupled to a distal tip of the manipulation member and extends distally from the distal tip.

26. The system of claim 13, wherein the intervention member comprises a thrombus removal device.

* * * * *